United States Patent
Mayer et al.

(10) Patent No.: US 7,514,411 B2
(45) Date of Patent: Apr. 7, 2009

(54) ACYLATED BENZYLMALTOSIDES AS INHIBITORS OF SMOOTH MUSCLE CELL PROLIFERATION

(75) Inventors: Scott C. Mayer, Robbinsville, NJ (US); Robert E. McDevitt, Somerset, NJ (US); Paul J. Dollings, Newtown, PA (US)

(73) Assignee: Wyeth, Madison, NJ (US)

( * ) Notice: Subject to any disclaimer, the term of this patent is extended or adjusted under 35 U.S.C. 154(b) by 70 days.

(21) Appl. No.: 11/505,543

(22) Filed: Aug. 17, 2006

(65) Prior Publication Data

US 2006/0276429 A1 Dec. 7, 2006

Related U.S. Application Data

(62) Division of application No. 10/699,233, filed on Oct. 31, 2003, now Pat. No. 7,132,402, which is a division of application No. 09/447,003, filed on Nov. 22, 1999, now abandoned.

(60) Provisional application No. 60/229,347, filed on Nov. 24, 1998.

(51) Int. Cl.
*A61K 31/702* (2006.01)
*C07H 15/203* (2006.01)

(52) U.S. Cl. .............. 514/25; 514/24; 536/4.1; 536/17.2; 536/123.13

(58) Field of Classification Search .......... None
See application file for complete search history.

(56) References Cited

U.S. PATENT DOCUMENTS

| | | | |
|---|---|---|---|
| 2,752,334 A | 6/1956 | Walton | |
| 4,431,637 A | 2/1984 | Upeslacis et al. | |
| 4,895,838 A | 1/1990 | McCluer et al. | |
| 4,912,093 A | 3/1990 | Michaeli | |
| 5,019,562 A | 5/1991 | Folkman et al. | |
| 5,037,973 A | 8/1991 | Meinetsberger | |
| 5,296,588 A | 3/1994 | Au et al. | |
| 5,310,542 A | 5/1994 | Au et al. | |
| 5,336,765 A | 8/1994 | Au et al. | |
| 5,464,827 A | 11/1995 | Soll | |
| 5,498,775 A | 3/1996 | Novak et al. | |
| 5,565,432 A | 10/1996 | Novak et al. | |
| 5,773,420 A | 6/1998 | Nguyen et al. | |
| 6,143,730 A | 11/2000 | Parish et al. | |
| 6,340,670 B1 * | 1/2002 | Mayer et al. .......... | 514/25 |

2004/0092457 A1 5/2004 Mayer et al.

FOREIGN PATENT DOCUMENTS

| | | |
|---|---|---|
| EP | 0312086 | 4/1989 |
| EP | 0312087 | 4/1989 |
| EP | 0356275 | 2/1990 |
| EP | 0454220 | 10/1991 |
| EP | 0550106 | 7/1993 |
| EP | 0551675 | 7/1993 |
| WO | WO 9006755 | 6/1990 |
| WO | WO 9309790 | 5/1993 |
| WO | WO 96/14325 | 5/1996 |
| WO | WO 9614324 | 5/1996 |
| WO | WO 9614325 | 5/1996 |

OTHER PUBLICATIONS

Hughes, Sian E., "Functional Characterization of the Spontaneously Transformed Human Umbilical vein Endothelial Cell Line ECV304: Use in an In Vitro Model of Angiogenesis", *Experimental Cell Research*, vol. 225, Article No. 0168, pp. 171-185 (1996).
Zehavi, et al., Carbohydrate Research, 1983, 124, 23-34.
Zehavi, et al., Carbohydrate Research, 1992, 228, 255-263.
Connors, et al., Herba Polonica, 1998, 44, 33-38.
Morales, et al., Angew, Chem. Int. Ed., 1988, 37(5), 654-657.
Zehavi, Carbohyd. Res., 1986, 151, 371.
Reilly, et al., Drug Development Research, 1993, 29, 137.
Klein, et al., Liebigs Ann. Chem., 1987, 485-489.
Durette, et al., Carbohydrate Research, 1978, 67, 484-490.
Bertho, Liebigs Ann. Chem., 1949, 562, 229-239.
Kopper, et al., Carbohydrate Research, 1989, 193, 296-302.

* cited by examiner

*Primary Examiner*—Leigh C Maier
(74) *Attorney, Agent, or Firm*—Fish & Richardson P.C.

(57) ABSTRACT

This invention provides smooth muscle cell proliferation inhibitors of formula I having the structure

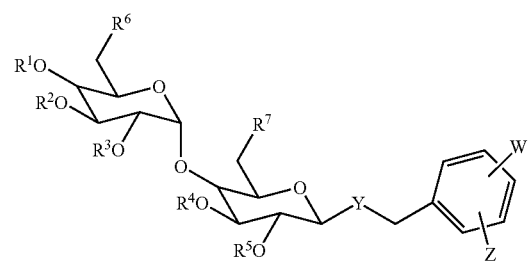

wherein $R^1$, $R^2$, $R^3$, $R^4$, $R^5$, $R^6$, $R^7$, W, Y, and Z are defined herein; or a pharmaceutically acceptable salt thereof.

6 Claims, No Drawings

ACYLATED BENZYLMALTOSIDES AS INHIBITORS OF SMOOTH MUSCLE CELL PROLIFERATION

This application is a divisional of U.S. application Ser. No.: 10/699,233 filed on Oct. 31, 2003 now U.S. Pat. No. 7,132, 402, which is a divisional of U.S. application Ser. No. :09/ 447,003, filed Nov. 22, 1999 (Now Abandoned), which claims the benefit of U.S. Provisional Application No. 60/229,347, which was converted from U.S. patent application Ser. No. 09/198,804, filed Nov. 24, 1998, pursuant to a petition filed under 37 C.F.R. 1.53(c)(2)(i). The entire contents of each of these prior applications are incorporated herein by reference.

BACKGROUND OF THE INVENTION

This invention relates to the use of substituted acylated benzylmaltosides as smooth muscle cell proliferation inhibitors and as therapeutic compositions for treating diseases and conditions which are characterized by excessive smooth muscle proliferation such as restenosis.

All forms of vascular reconstruction such as angioplasty and vein bypass procedures effect a response to injury that ultimately leads to smooth muscle cell (SMC) proliferation and subsequently, deposition of profuse amounts of extracellular matrix (Clowes, A. W.; Reidy, M. A. *J. Vasc. Surg* 1991, 13, 885). These events are also central processes in the pathogenesis of atherosclerosis (Raines E. W.; Ross R. *Br. Heart J.* 1993, 69 (Supplement), S. 30) as well as transplant arteriosclerosis (Isik, F. F.; McDonald, T. O.; Ferguson, M.; Yamanaka, E.; Gordon *Am. J. Pathol.* 1992, 141, 1139). In the case of restenosis following angioplasty, clinically relevant solutions for controlling SMC proliferation through pharmacological intervention have remained elusive to date (Herrman, J. P. R.; Hermans, W. R. M.; Vos, J.; Serruys P. W. *Drugs* 1993, 4, 18 and 249). Any successful approach to selective SMC proliferation inhibition must not interfere with endothelial cell repair or the normal proliferation and function of other cells (Weissberg, P. L.; Grainger, D. J.; Shanahan C. M.; Metcalfe, J. C. *Cardiovascular Res.* 1993, 27, 1191).

The glycosaminoglycans heparin and heparan sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13, 489). However, the full clinical benefits of heparin, heparin fragments, chemically modified heparin, low molecular weight heparins, and other heparin mimicking anionic polysaccharides may be compromised due to other pharmacological liabilities (excessive bleeding arising from anticoagulation effects, in particular) coupled with heterogeneity of the various preparations (Borman, S. *Chemical and Engineering News,* 1993, Jun. 28, 27).

WO 96/14325 discloses acylated benzylglycosides as smooth muscle cell proliferation inhibitors. The compounds of the present invention differ in that the substituents on the carbohydrate backbone are different.

Zehavi, U.; Herchman, M. in *Carbohyd. Res.* 1986, 151, 371, disclosed 4-carboxy-2-nitrobenzyl 4-O-α-D-glucopyranosyl-β-D-glucopyranoside which is attached to a polymer for study as an acceptor in the glycogen synthase reaction. The compounds of the present invention differ in that the substituents on the benzyl groups are different and the use (smooth muscle antiproliferation) is different.

Patent numbers U.S. Pat. No. 5,498,775, WO96/14324, and U.S. Pat. No. 5,464,827 describe polyanionic benzylglycosides or cyclodextrins as smooth muscle cell proliferation inhibitors for treating diseases and conditions which are characterized by excessive smooth muscle proliferation. β-cyclodextrin tetradecasulfate has been described as a smooth muscle cell proliferation inhibitor and as an effective inhibitor of restenosis (Reilly, C. F.; Fujita, T.; McFall, R. C.; Stabilito, I. I.; Wai-se E.; Johnson, R. G. *Drug Development Research* 1993, 29, 137). U.S. Pat. No. 5,019,562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residues. Meinetsberger (EP 312087 A2 and EP 312086 A2) describes the antithrombotic and anticoagulant properties of sulfated bis-aldonic acid amides. U.S. Pat. No. 4,431,637 discloses polysulfated phenolic glycosides as modulators of the complement system. The compounds of the present invention differ from all of the prior art in that the compounds (a) are benzylmaltosides which bear no structural resemblance to heparin, sulfated cyclodextrins, or to sulfated lactobionic acid dimers, (b) contain no more than two contiguous sugar residues (disaccharide), (c) are of a defined structure, (d) and are not sulfated.

DESCRIPTION OF THE INVENTION

This invention provides benzylmaltosides of formula I

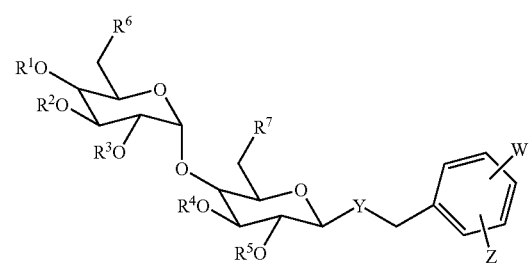

wherein
$R^1$, $R^2$, $R^3$, $R^4$, and $R^5$ are each, independently, hydrogen, acyl of 2-7 carbon atoms, haloacyl of 2-7 carbon atoms, nitroacyl of 2-7 carbon atoms, cyanoacyl of 2-7 carbon atoms, trifluoromethylacyl of 3-8 carbon atoms, or benzoyl in which the phenyl moiety is substituted with $R^8$;
$R^6$ and $R^7$ are each, independently, —OH, —OR$^9$, O-tert-butyldimethylsilyl, O-trialkylsilyl of 1-6 carbon atoms per alkyl moiety, O-triphenylsilyl,

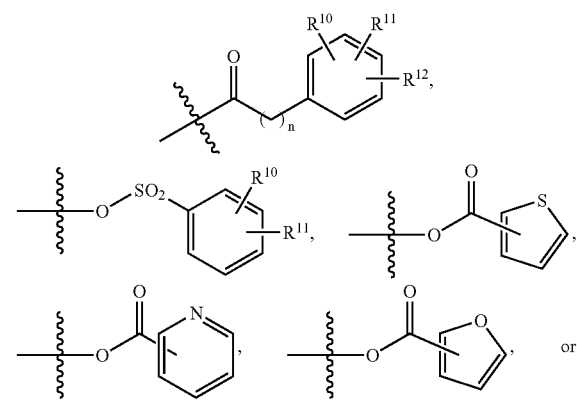

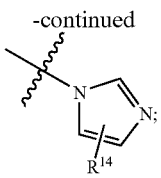

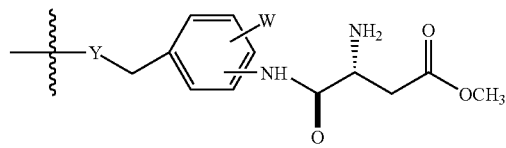

$R^8$, $R^{10}$, $R^{11}$, and $R^{12}$ are each, independently, hydrogen, —CN, —NO$_2$, halogen, CF$_3$, alkyl of 1-6 carbon atoms, acetyl, benzoyl, or alkoxy of 1-6 carbon atoms;

$R^9$ is acyl of 2-7 carbon atoms, haloacyl of 2-7 carbon atoms, nitroacyl of 2-7 carbon atoms, cyanoacyl of 2-7 carbon atoms, trifluoromethylacyl of 3-8 carbon atoms, or benzoyl in which the phenyl moiety is substituted with $R^8$;

Y is O, S, NH, NMe, or CH$_2$;

W is halogen, —CN, CF$_3$, alkyl of 1-6 carbon atoms, haloalkyl of 1-6 carbon atoms, nitroalkyl of 1-6 carbon atoms, cyanoalkyl of 1-6 carbon atoms, alkoxyalkyl of 2-12 carbon atoms, alkoxy of 1-6 carbon atoms, or phenyl mono-, di-, or tri-substituted with $R^8$;

Z is —NO$_2$, —NH$_2$, —NHR$^{13}$, or —NHCO-Het;

$R^{13}$ is acyl of 2-7 carbon atoms, haloacyl of 2-7 carbon atoms, nitroacyl of 2-7 carbon atoms, cyanoacyl of 2-7 carbon atoms, trifluoromethylacyl of 3-8 carbon atoms, benzoyl in which the phenyl moiety is substituted with $R^8$, or $R^{13}$ is an α-amino acid in which the a carboxyl group forms an amide with the nitrogen of Z, wherein if said amino acid is glutamic acid or aspartic acid, the non-α carboxylic acid is an alkyl ester in which the alkyl moiety contains from 1-6 carbon atoms;

Het is pyridyl substituted with $R^8$, thienyl substituted with $R^8$, furyl substituted with $R^8$, oxazolyl substituted with $R^8$, pyrazinyl substituted with $R^8$, pyrimidinyl substituted with $R^8$, or thiazolyl substituted with $R^8$;

$R^{14}$ is $R^8$, —NH$_2$, —CO$_2$H, or —NH-acyl of 2-7 carbon atoms;

n=0-3;

with the proviso that when Z is —NHR$^{13}$ and Y is O, at least one of $R^1$, $R^2$, $R^3$, $R^4$, and $R^5$ is hydrogen, or at least one of $R^6$ and $R^7$ is OH, or a pharmaceutically acceptable salt thereof.

Alkyl includes both straight chain as well as branched moieties. Halogen means bromine, chlorine, fluorine, and iodine. When $R^{13}$ is an α-amino acid, the carboxyl moiety exists as an amide with the amide nitrogen being bonded to the phenyl ring of the compound of formula I. The following exemplifies the resulting structure when $R^{13}$ is alanine:

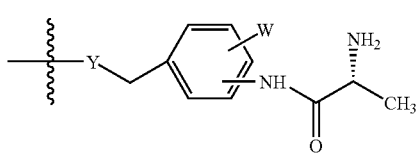

When the amino acid contains a second carboxyl moiety, the moiety is an alkyl ester of the free acid. The following example shows aspartic acid methyl ester.

Preferred amino acids include alanine, arginine, aspartic acid, cystine, glutamic acid, glycine, histidine, isoleucine, leucine, lysine, methionine, phenylalanine, proline, serine, threonine, tryptophan, tyrosine, and valine. The amino acids defined by $R^{13}$ include both the D and L amino acids.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from organic and inorganic bases, preferably alkali metal salts, for example, sodium, lithium, or potassium. Acid addition salts can be prepared when Y contains a nitrogen or the compound of formula I contains a basic nitrogen, and base addition salts can typically be prepared when the compound of formula I contains a hydroxyl group.

The compounds of this invention may contain an asymmetric carbon atom or sulfoxide moiety and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds of this invention are benzylmaltosides of formula I

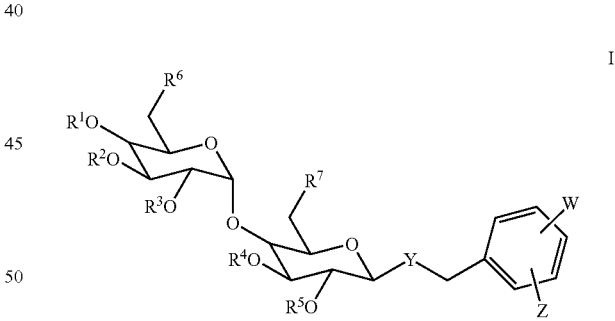

wherein $R^1$, $R^2$, $R^3$, $R^4$, and $R^5$ are each, independently, hydrogen or acyl of 2-7 carbon;

$R^6$ and $R^7$ are each, independently, —OH, —OR$^9$, O-tert-butyldimethylsilyl,

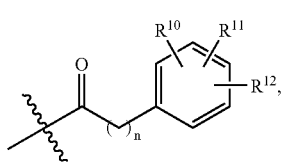

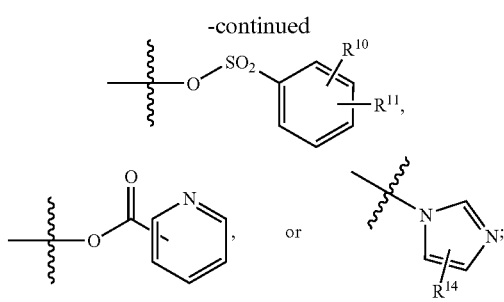

$R^8$, $R^{10}$, $R^{11}$, and $R^{12}$ are each, independently, hydrogen, —CN, —NO$_2$, halogen, CF$_3$, alkyl of 1-6 carbon atoms, acetyl, benzoyl, or alkoxy of 1-6 carbon atoms;

$R^9$ is acyl of 2-7 carbon atoms, or benzoyl in which the phenyl moiety is substituted with $R^8$;

Y is O or S;

W is halogen, or alkyl of 1-6 carbon atoms, haloalkyl of 1-6 carbon atoms, nitroalkyl of 1-6 carbon atoms, cyanoalkyl of 1-6 carbon atoms, alkoxyalkyl of 2-12 carbon atoms, alkoxy of 1-6 carbon atoms, or phenyl mono-, di-, or tri-substituted with $R^8$;

Z is —NO$_2$, —NH$_2$, —NHR$^{13}$, or —NHCO-Het;

$R^{13}$ is acyl of 2-7 carbon atoms, or benzoyl in which the phenyl moiety is substituted with $R^8$, or $R^{13}$ is an α-amino acid in which the a carboxyl group forms an amide with the nitrogen of Z, wherein if said amino acid is glutamic acid or aspartic acid, the non-α carboxylic acid is an alkyl ester in which the alkyl moiety contains from 1-6 carbon atoms;

Het is pyridyl substituted with $R^8$, thienyl substituted with $R^8$, furyl substituted with $R^8$, oxazolyl substituted with $R^8$, pyrazinyl substituted with $R^8$, pyrimidinyl substituted with $R^8$, or thiazolyl substituted with $R^8$;

$R^{14}$ is $R^8$, —NH$_2$, —CO$_2$H, or —NH-acyl of 2-7 carbon atoms;

n=0-3;

with the proviso that when Z is —NHR$^{13}$ and Y is O, at least one of $R^1$, $R^2$, $R^3$, $R^4$, and $R^5$ is hydrogen, or at least one of $R^6$ and $R^7$ is OH, or a pharmaceutically acceptable salt thereof.

Specifically preferred compounds of this invention are:.

4-Chloro-3-nitro-benzyl-β-D-maltoside heptaacetate or a pharmaceutically acceptable salt thereof;

N-{5-[(Hepta-O-acetyl-β-D-maltosyloxy)-methyl]-2-chloro-phenyl}-L-aspartamidle-γ-tert-butyl ester or a pharmaceutically acceptable salt thereof;

N-{2-Chloro-5-[(2,2',3,3',4',6,6')-hepta-O-acetyl-β-D-maltosyl-oxymethyl]-phenyl}-(9H-fluoren-9-ylmethoxycarbonyl)-L-alaninamide or a pharmaceutically acceptable salt thereof;

4-Benzoyl-N-{2-chloro-5-[(2,2',3,3 ',4',6,6'-hepta-O-acetyl-β-D-maltosyl)-oxy-methyl]-phenyl}-benzamide or a pharmaceutically acceptable salt thereof;

(4-Chloro-3-nitro-benzyl)-hepta-O-acetyl-1-thio-β-D-maltoside or a pharmaceutically acceptable salt thereof;

(3-Amino-4-chloro-benzyl) hepta-O-acetyl-1-thio-β-D-maltoside or a pharmaceutically acceptable salt thereof;

N-{2-chloro-5-[hepta-O-acetyl-β-D-maltosyl-1-thio)-methyl]-phenyl}-acetamide or a pharmaceutically acceptable salt thereof;

5-[(Hepta-O-acetyl-β-D-maltosyl)-oxy-methyl]-2-cyano-1-nitrobenzene or a pharmaceutically acceptable salt thereof.

N-[2-Chloro-5-(β-D-maltosyl-oxymethyl)-phenyl]-acetantide or a pharmaceutically acceptable salt thereof;

N-{5-[6,6'-Di-O-(tert-butyl-dimethyl-silyl)-β-D-maltosyloxy-methyl]-2-methyl-phenyl}-acetamide or a pharmaceutically acceptable salt thereof;

N-{2-Chloro-5-[6,6'-di-O-(tert-butyl-dimethyl-silyl)-β-D-maltosyloxy-methyl]-phenyl}-acetamide or a pharmaceutically acceptable salt thereof;

N-{2-Chloro-5-[([6,6'-di-O-benzoyl-β-D-maltosyl]oxy)methyl]phenyl}-acetamide or a pharmaceutically acceptable salt thereof;

N-{2-Chloro-5-[([6,6'-di-O-benzoyl-2,2',3,3',4'-penta-acetyl-β-D-maltosyl]oxy)-methyl]phenyl}-acetamide or a pharmaceutically acceptable salt thereof;

(4-Chloro-3-nitrophenyl)methyl-4-O-[6-O-(3-pyridinylcarbonyl)-α-D-glucopyranosyl]-β-D-glucopyranoside-6-(3-pyridinecarboxylate) or a pharmaceutically acceptable salt thereof;

(4-Chloro-3-nitrophenyl)methyl-4-O-[6-O-(3-pyridinylcarbonyl)-α-D-glucopyranosyl]-β-D-glucopyranoside or a pharmaceutically acceptable salt thereof;

N-[2-Chloro-5-[[(4-O-α-D-glucopyranosyl-β-D-glucopyranosyl)oxy]methyl]phenyl]-3-pyridinecarboxamide or a pharmaceutically acceptable salt thereof;

Benzoic acid 6-{4-chloro-3-[(pyridine-3-carbonyl)-amino]-benzyloxy}-4,5-dihydroxy-3-(3,4,5-trihydroxy-6-hydroxymethyl-tetrahydro-pyran-2-yloxy)-tetrahydro-pyran-2-ylmethyl ester or a pharmaceutically acceptable salt thereof;

(4-Chloro-3-nitro-benzyl)-1-deoxy-1-thio-β-D-maltoside or a pharmaceutically acceptable salt thereof;

N-{2-chloro-5-[β-D-maltosyl-1-thio)-methyl]-phenyl}-acetamide or a pharmaceutically acceptable salt thereof;

5-{[6,6'-Bis-O-(4-toluenesulfonyl)-β-maltosyl]-oxy-methyl}-2-methyl-1-nitrobenzene or a pharmaceutically acceptable salt thereof;

5-{[2,2',3,3 ',4'-Penta-O-acetyl-6,6'-bis-O-(4-toluenesulfonyl)-β-maltosyl]-oxy-methyl}-2-methyl-1-nitrobenzene or a pharmaceutically acceptable salt thereof;

5-{[6,6'-Dideoxy-6,6'-bis(4-nitro-imidazol-1-yl)-β-maltosyl]-oxy-methyl}-2-methyl-1-nitrobenzene or a pharmaceutically acceptable salt thereof; and 5-{[2,2',3,3',4'-Penta-O-acetyl-6,6'-dideoxy-6,6'-bis(4-nitro-imidazol-1-yl)-β-maltosyl]-oxy-methyl}-2-methyl-1-nitrobenzene or a pharmaceutically acceptable salt thereof.

The compounds of this invention were be prepared according to the following schemes from commercially available starting materials or starting materials which can be prepared using literature procedures. These schemes show the preparation of representative compounds of this invention.

Acetobromomaltose 1 is coupled with a benzyl alcohol 2 in the presence of a catalyst such as a mercuric bromide, mercuric cyanide, silver triflate, or silver perchlorate in an aprotic solvent such as acetonitrile, dichloromethane, ether, toluene or nitromethane at temperatures ranging from −40° C. to reflux to yield glycoside 3 (Scheme 1). This glycosidation can also be accomplished using Schmidt's trichloroacetimidate coupling with zinc bromide in a solvent such as dichloromethane. Reduction of the nitro group of 3 can be accomplished with a reducing agent such as stannous chloride in a polar aprotic solvent such as ethyl acetate at ambient temperature to reflux to afford an anilino compound 4. Coupling of 4 with an acid chloride can be completed in the presence of an amine base such as triethylamine or diisopropylethylamine or using a stronger base such as sodium hydride (for sterically hindered systems) in an aprotic solvent such as dichloromethane or tetrahydrofuran at temperatures ranging from 0° C. to ambient temperature to yield the target compound 5. The peracetylated compound 5 can be converted to the heptahydroxy compound 6 with catalytic sodium methoxide in methanol or aqueous sodium hydroxide in methanol at temperatures ranging from ambient temperature to reflux.

As illustrated in Scheme 2, the C-6 and C-6' positions can be selectively protected as a silyl ether (7) using t-butyldimethylchlorosilane, a tertiary base such as triethylamine, and a catalytic amount of 4-dimethylaminopyridine. In addition, the 6- and 6'-position primary alcohols can be selectively acylated (Scheme 3) using an appropriate acid chloride in a 1:1 mixture of tetrahydrofuran and the hindered base 2,4,6-collidine at −40° C. initially to ambient temperature overnight. The remaining five secondary alcohols of the disaccharide can then be protected with acetic anhydride and triethylamine in a solvent such as dichloromethane to afford the peracetylated compound 8.

In Scheme 4 the two primary alcohol positions (C-6 and C-6') are first converted to tosylates using tosyl chloride and pyridine in a solvent such as dichloromethane; the resulting intermediate is then peracetylated as mentioned above to generate compound 9. Through displacement of the tosylates of 9, heterocyclic ring systems can be incorporated at the 6 and 6' positions. Finally, the five secondary acetates are removed with catalytic sodium methoxide in methanol or aqueous sodium hydroxide in methanol at temperatures ranging from ambient temperature to reflux to afford compound 10.

-continued

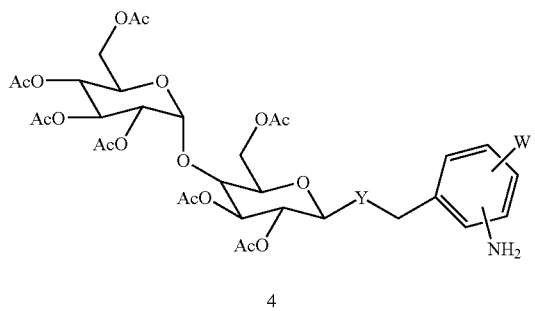

4

↓ acylation

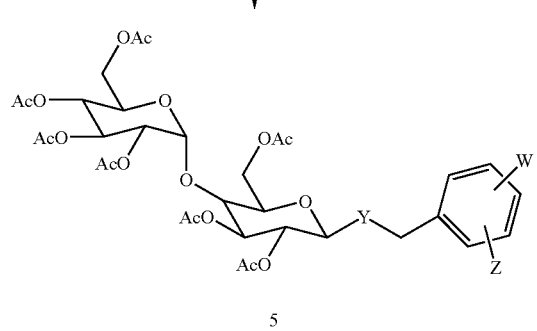

5

↓ hydrolysis

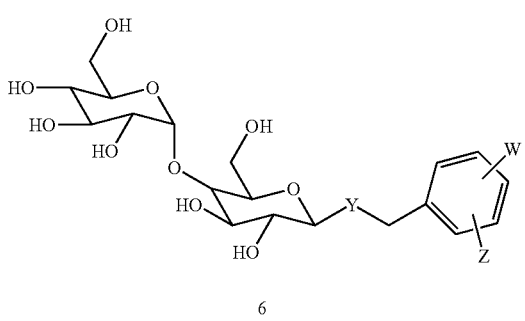

6

If R$_2$=OH or OTBDMS:

Scheme 2

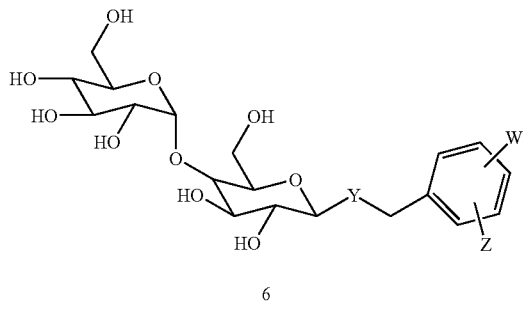

6

↓ silylation

Scheme 1

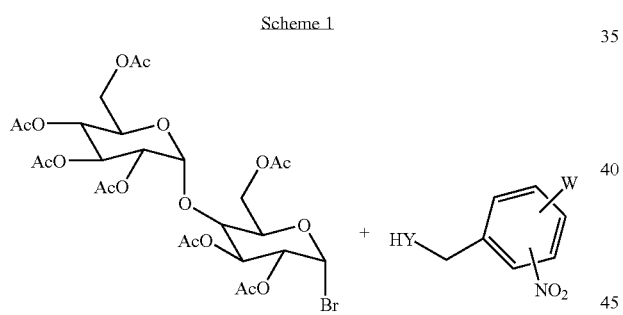

1 + 2

↓ glycosidation

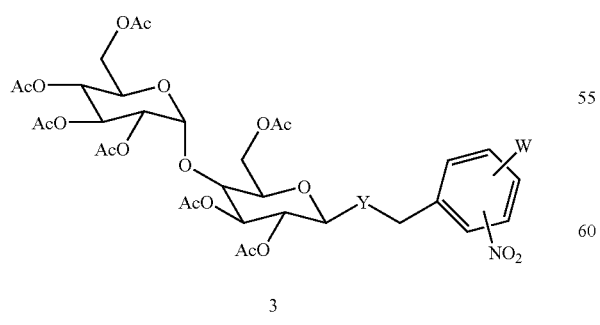

3

↓ reduction

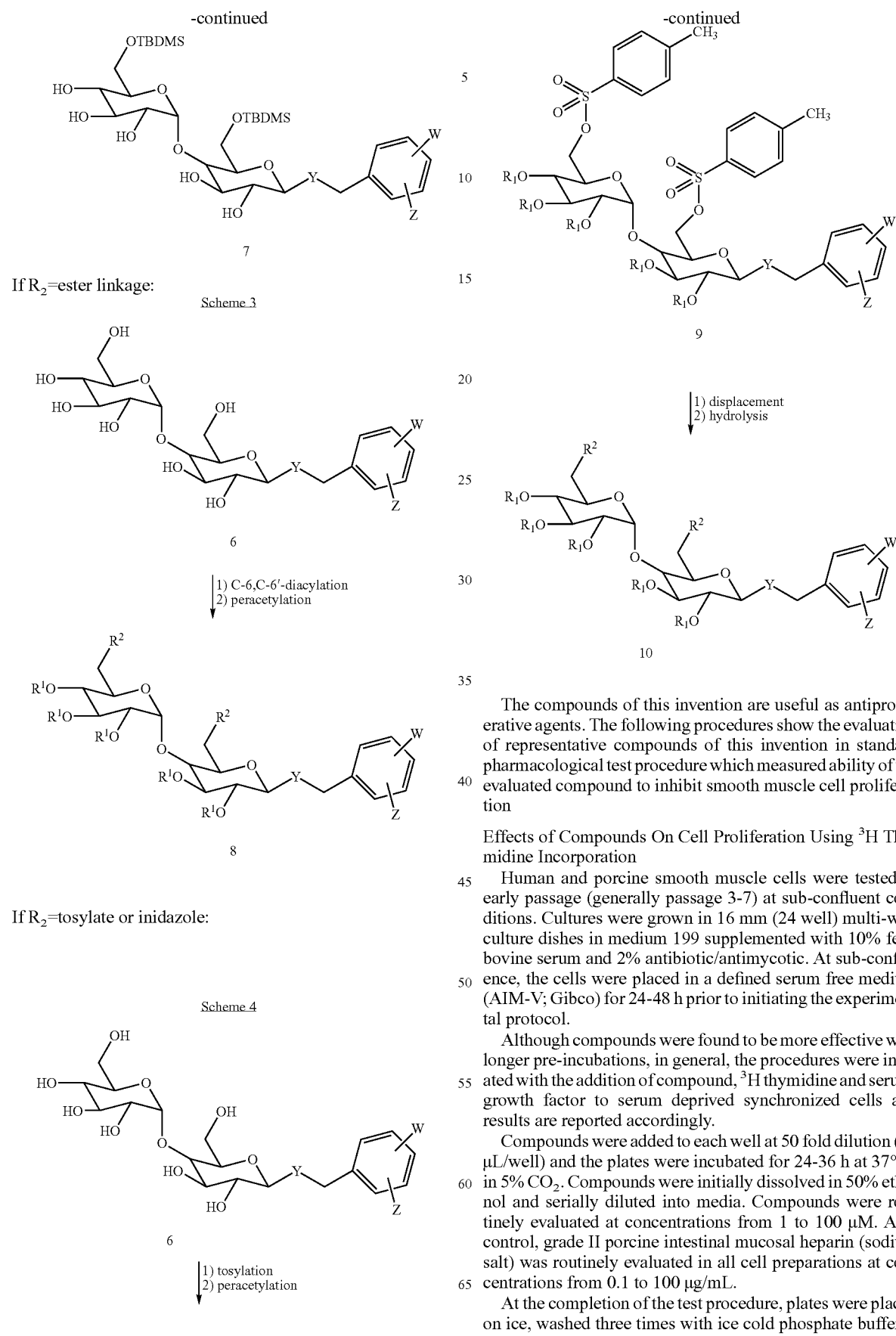

The compounds of this invention are useful as antiproliferative agents. The following procedures show the evaluation of representative compounds of this invention in standard pharmacological test procedure which measured ability of the evaluated compound to inhibit smooth muscle cell proliferation Effects of Compounds On Cell Proliferation Using $^3$H Thymidine Incorporation Human and porcine smooth muscle cells were tested in early passage (generally passage 3-7) at sub-confluent conditions. Cultures were grown in 16 mm (24 well) multi-well culture dishes in medium 199 supplemented with 10% fetal bovine serum and 2% antibiotic/antimycotic. At sub-confluence, the cells were placed in a defined serum free medium (AIM-V; Gibco) for 24-48 h prior to initiating the experimental protocol.

Although compounds were found to be more effective with longer pre-incubations, in general, the procedures were initiated with the addition of compound, $^3$H thymidine and serum/growth factor to serum deprived synchronized cells and results are reported accordingly.

Compounds were added to each well at 50 fold dilution (20 μL/well) and the plates were incubated for 24-36 h at 37° C. in 5% $CO_2$. Compounds were initially dissolved in 50% ethanol and serially diluted into media. Compounds were routinely evaluated at concentrations from 1 to 100 μM. As a control, grade II porcine intestinal mucosal heparin (sodium salt) was routinely evaluated in all cell preparations at concentrations from 0.1 to 100 μg/mL.

At the completion of the test procedure, plates were placed on ice, washed three times with ice cold phosphate buffered saline (PBS) and incubated in ice cold 10% trichloroacetic acid (TCA) got 30 min to remove acid soluble proteins. Solution was transferred to scintillation vials containing 0.4 N HCl (500 μL/vial to neutralize NaOH) and each well was rinsed two times with water (500 μL) for a total volume of 2 mL/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data are expressed as an $IC_{50}$ or percent inhibition in Table I below.

TABLE 1

| Compound of Example | Porcine Smooth Muscle Cell Antiproliferation IC50 |
| --- | --- |
| 1 | 0.850 μM |
| 2 | 4.61 μM |
| 3 | 1.71 μM |
| 4 | 0.164 μM |
| 5 | 1.14 μM |
| 6 | 0.667 μM |
| 7 | 7.97 μM |
| 8 | 2.05 μM |
| 9 | 0% @ 500 μM |
| 10 | 6.10 μM |
| 11 | 3.90 μM |
| 12 | 0.390–2.20 μM |
| 13 | 0.360 μM |
| 14 | 6.56 μM |
| 15 | 73.2 μM |
| 16 | 18% @ 50 μM |
| 17 | 0.245 μM |
| 18 | 25% @ 50 μM |
| 19 | 28% @ 50 μM |
| 20 | 0.740 μM |
| 21 | 67.4 μM |
| 22 | 23% @ 100 μM |
| 23 | 4.70 μM |

The compounds of this invention are useful in treating or inhibiting diseases which are characterized by excessive smooth muscle cell proliferation (smooth muscle cell hyperproliferation). The compounds are particularly useful in treating hyperproliferative vascular diseases which are characterized by smooth muscle cell hyperproliferation, such as restenosis, which most frequently arises from vascular reconstructive surgery and transplantation, for example, balloon angioplasty, vascular graft surgery, coronary artery bypass surgery, and heart transplantation. Other disease states in which there is unwanted "cellular" vascular proliferation include hypertension, asthma, and congestive heart failure. The compounds of this invention are also useful as inhibitors of angiogenesis. Angiogenesis (neovascularization), the process by which new capillaries are formed, is of principal importance for a number of pathological events including chronic inflammation and malignant processes. The compounds of this invention are therefore useful as antineoplastic agents.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.1 to 10 mg/kg administered parenterally (intravenous preferred), with projected daily oral dosage being approximately ten-fold higher. Anticipated intravenous administration would last for approximately 5-30 days following acute vascular injury (i.e., balloon angioplasty or transplantation) and for a longer duration for the treatment of chronic disorders. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of representative compounds of this invention.

EXAMPLE 1

4-Chloro-3-nitro-benzyl-β-D-maltoside heptaacetate

To a stirred solution of 4-chloro-3-nitrobenzyl alcohol (6.70 g, 35.7 mmol) and $HgBr_2$ (14.2 g, 39.3 mmol) in freshly distilled $CH_3CN$ (239 mL) was added in one portion $Hg(CN)_2$ (9.02 g, 35.7 mmol). After 0.5 h, acetobromomaltose (25.0 g, 35.7 mmol) was added, and the mixture stirred for 18 h at rt. The reaction was then quenched with a mixture of $H_2O$:brine (1:1, 100 mL) and extracted with 10% $CH_2Cl_2$:EtOAc. The combined organic extracts were dried ($MgSO_4$) and concentrated. Purification by flash chromatography (10:90 to 80:20 EtOAc:petroleum ether gradient) gave 51.9 g (90%) of the title compound as a glassy oil which was recrystallized from EtO:petroleum ether to afford a glassy white solid, mp 107-111° C.; $^1H$ NMR ($CDCl_3$) δ 2.00 (s, 3H), 2.02 (s, 3H), 2.03, (s, 3H), 2.04 (s, 6H), 2.11 (s, 3H), 2.15 (s, 3H), 3.70 (ddd, J=2.9, 4.2, 9.7 Hz, 1H), 3.94-3.98 (m, 1H), 4.01-4.07 (m, 2H), 4.20-4.28 (m, 2H), 4.54 (dd, J=2.9, 12.3 Hz, 1H), 4.63-4.68 (m, 2H), 4.84-4.94 (m, 3H), 5.06 (t, J=10.1 Hz, 1H), 5.26 (t, J=9.2 Hz, 1H), 5.36 (dd, J=9.7, 10.3 Hz, 1H), 5.42 (d, J=4.2 Hz, 1H), 7.43 (dd, J=2.2, 8.3 Hz, 1H), 7.53 (d, J=8.3 Hz, 1H), 7.83 (d, J=2.0 Hz, 1H); IR (KBr) 3450, 2950, 1755, 1550, 1375, 1230 and 1050 cm$^{-1}$; mass spectrum [(+) ESI], m/z 823/825 (M+$NH_4^+$), 828/830 (M+Na)$^+$; Anal. Calcd. for $C_{33}H_{40}ClNO_{20}$: C, 49.17; H, 5.00; N, 1.74, Found: C, 49.16; H, 4.88; N. 1.71.

EXAMPLE 2

N-{5-[(Hepta-O-acetyl-β-D-maltosyloxy)-methyl]-2-chloro-phenyl}-L-aspartamide-γ-tert-butyl ester Step 1

2-Chloro-5-(hepta-O-acetyl-β-D-maltosyl-oxymethyl)-phenylamine

A solution containing 4-chloro-3-nitro-benzyl-β-D-maltoside heptaacetate (Example 1, 19.3 g, 23.9 mmol) and tin (II) chloride dihydrate (37.7 g, 167 mmol) in EtOAc (479 mL) was refluxed for 2 h. The reaction was cooled to rt, carefully quenched with sat. aq. $NaHCO_3$ (until basic), diluted with EtOAc (250 mL), stirred for 0.5 h and filtered. The biphasic filtrate was separated and the aqueous phase extracted with EtOAc. The combined organic extracts were dried ($Na_2SO_4$) and concentrated. Purification by flash chromatography (0 to 12% acetone/$CHCl_3$ gradient) gave 17.8 g (96%) 2-Chloro-5-(hepta-O-acetyl-β-D-maltosyl-oxymethyl)-phenylamine as a glassy solid, mp 78-79° C.; $^1H$ NMR ($CDCl_3$) δ 2.00 (s, 9H), 2.026 (s, 3H), 2.032 (s, 3H), 2.11 (s, 3H), 2.16 (s 3H), 3.00-5.00 (bs, 2H), 3.64-3.68 (m, 1H), 3.97 (ddd, J=2.4, 4.2, 10.1 Hz, 1H), 4.02-4.07 (m, 2H), 4.24 (dd, J=2.2, 3.7, 1H), 4.27 (dd, J=2.6, 4.0 Hz, 1H), 4.50-4.57 (m, 3H), 4.74 (d, J=12.1 Hz, 1H), 4.83-4.90 (m, 2H), 5.05 (t, J=10.1 Hz, 1H), 5.22 (t, J=9.2 Hz, 1H), 5.35 (dd, J=9.7, 10.5 Hz, 1H), 5.42 (d, J=4.0 Hz, 1H), 6.62 (dd, J=2.0, 8.1 Hz, 1H), 6.76 (d, J=2.0 Hz, 1H), 7.21 (d, J=8.1, 1H); IR (KBr) 3450, 3350, 2950, 1755, 1650, 1425, 1375, 1230 and 1050 cm$^{-1}$; mass spectrum [(+) ESI], m/z 776/778 (M+H)$^+$, 798/800 (M+Na)$^+$; Anal. Calcd. for $C_{33}H_{42}ClNO_{18}$: C, 51.07; H, 5.45; N, 1.80, Found: C, 50.94; H, 5.52; N, 1.60.

Step 2

N-{5-[(Hepta-O-acetyl-β-D-maltosyloxy)-methyl]-2-chloro-phenyl}-(9H-fluoren-9-ylmethyoxycarbonylamino)-L-aspartamide-4-tert-butyl ester To a stirred solution of N-(9H-fluoren-9-ylmethyoxycarbonylamino)-L-aspartic acid-4-tert-butyl ester (0.117 g, 0.284 mmol) and DMF (cat. amt.) in $CH_2Cl_2$ (3 mL) at rt was added oxalyl chloride (24.8 μL, 0.284 mmol) dropwise. After 5 min. at this temperature, it was heated to 40° C. for an additional 10 min. This completed the preparation of the acid chloride starting material. At this point, to a second stirred solution of NaH (0.0103 g, 0.258 mmol) and $CH_2Cl_2$ (4 mL) at rt was added 2-chloro-5-(hepta-O-acetyl-β-D-maltosyl-oxymethyl)-phenylamine (0.200 mg, 0.258 mmol). After 10 min., the acid chloride solution was added to this solution dropwise. The reaction was stirred at rt for 1 h and then diluted with EtOAc (100 mL). This layer was washed with 1N HCl (10 mL), sat. $NaHCO_3$ (10 mL), and brine (10 mL) and then dried ($MgSO_4$). After concentration, the oilly residue was purified by flash chromatography (10:90 to 70:30 EtOAc: petroleum ether gradient) to afford the product (0.157 g, 52%) as a white foam, mp 103-105° C.; $^1H$ NMR ($CDCl_3$) δ 1.46 (s, 9H), 1.99 (s, 3H), 2.00 (s, 3H), 2.01 (s, 3H), 2.02 (s, 3H), 2.03 (s, 3H), 2.10 (s, 3H), 2.16 (s, 3H), 2.70 (dd, J=5.9, 17.4 Hz, 1H), 2.96-3.06 (m, 1H), 3.67 (ddd, J=2.6, 4.2, 9.7 Hz, 1H), 3.96 (ddd, J=2.4, 3.7, 10.3 Hz, 1H), 4.00-4.06 (m, 2H), 4.22-4.28 (m, 3H), 4.42-4.48 (m, 1H), 4.48-4.56 (m, 2H), 4.58 (dd, J=2.2, 10.1 Hz, 2H), 4.68-4.76 (m, 1H), 4.81-4.91 (m, 3H), 5.05 (t, J=10.1 Hz, 1H), 5.22 (t, J=9.2 Hz, 1H), 5.35 (dd, J=9.7, 10.5 Hz, 1H), 5.41 (d, J=4.0 Hz, 1H), 6.07-6.15 (m, 1H), 7.00 (dd, J=2.0, 8.1 Hz, 1H), 7.28-7.36 (m, 3H), 7.40 (t, J=7.2 Hz, 2H), 7.57-7.62 (m, 2H), 7.77 (d, J=7.5 Hz, 2H), 8.31 (d, J=1.8 Hz, 1H), 8.86 (s, 1H); IR (KBr) 3380, 2960, 1755, 1600, 1540, 1440, 1420, 1375, 1230, 1160, and 1050 cm$^{-1}$; mass spectrum [(+) FAB], m/z 1169 (M+H)$^+$, 1191 (M+Na)$^+$; Anal. Calcd. for $C_{56}H_{65}ClN_2O_{23}·2.0\ H_2O$: C, 55.79; H, 5.77; N, 2.32, Found: C, 55.89; H, 5.45; N, 2.25.

Step 3

N-{5-[(Hepta-O-acetyl-β-D-maltosyloxy)-methyl]-2-chloro-phenyl}-L-aspartamide-γ-tert-butyl ester To a stirred solution of 20% piperidine (2.00 mL, 20.2 mmol) in DMF (10 mL) at rt was added N-{5-[(hepta-O-acetyl-β-D-maltosyloxy)-methyl]-2-chloro-phenyl}-(9H-fluoren-9-ylmethyoxycarbonylamino)-L-aspartamide-4-tert-butyl ester (0.300 g, 0.256 mmol). After 1 h at this temperature, the solution was concentrated on the high vacuum. At this point, the residue was diluted with cold $H_2O$ (20 mL) and then extracted with $Et_2O$ (50 mL). This layer was dried ($Na_2SO_4$) and after concentration, the resulting oil was purified by flash chromatography (20:80 to 90:10 EtOAc:

petroleum ether gradient) to afford the product (0.186 g, 77%) as a white solid, mp 85-87° C.; $^1$H NMR (CDCl$_3$) δ 1.45 (s, 9H), 1.89 (s, 2H), 1.99 (s, 6H), 2.01 (s, 3H), 2.02 (s, 3H), 2.03 (s, 3H), 2.10 (s, 3H), 2.16 (s, 3H), 2.68 (dd, J=8.1,.16.7 Hz, 1H), 2.91 (dd, J=3.7, 16.7 Hz, 1H), 3.64-3.69 (m, 1H), 3.80 (dd, J=3.7, 8.3 Hz, 1H), 3.93-3.98 (m, 1H), 3.99-4.05 (m, 2H), 4.21-4.27 (m, 2H), 4.50 (dd, J=2.6, 12.1 Hz, 1H), 4.56 (d, J=3.7 Hz, 1H), 4.59 (d, J=8.1 Hz, 1H), 4.81-4.91 (m, 3H), 5.05 (t, J=10.1 Hz, 1H), 5.22 (t, J=9.4 Hz, 1H), 5.34 (dd, J=9.4, 10.3 Hz, 1H), 5.40 (d, J=4.0 Hz, 1H), 6.98 (dd, J=2.0, 8.1 Hz, 1H), 7.34 (d, J=8.1 Hz, 1H), 8.42 (d, J=2.0 Hz, 1H), 10.28 (s, 1H); IR (KBr) 3380, 2960, 1755, 1600, 1540, 1440, 1420, 1375, 1235, 1140, and 1040 cm$^{-1}$; mass spectrum [(+) FAB], m/z 947/949 (M+H)$^+$, 969/971 (M+Na)$^+$; Anal. Calcd. for C$_{41}$H$_{55}$ClN$_2$O$_{21}$: C, 51.98; H, 5.85; N, 2.96, Found: C, 51.62; H, 5.89; N, 2.95.

EXAMPLE 3

N-{2-Chloro-5-[(2,2',3,3',4',6,6')-hepta-O-acetyl-β-D-maltosyl-oxymethyl]-phenyl}-(9H-fluoren-9-yl-methoxycarbonyl)-L-alaninamide The title compound was prepared as a white foam (2.50 g, 36%) from 2-chloro-5-(hepta-O-acetyl-β-D-maltosyl-oxymethyl)-phenylamine using N-(9H-fluoren-9-ylmethyoxycarbonylamino)-L-alanine and a procedure similar to step 2 of Example 2, mp >96° C. (decomp.); $^1$H NMR (DMSO-d$_6$) δ 1.33 (dd, J=7.2 Hz, 3H), 1.918 (s, 3H), 1.919 (s, 3H), 1.94 (s, 3H), 1.966 (s, 3H), 1.97 (s, 3H), 2.01 (s, 3H), 2.07 (s, 3H), 3.91-4.02 (m, 4H), 4.12-4.24 (m, 3H), 4.24-4.34 (m, 3H), 4.34-4.40 (m, 1H), 4.53 (d, J=12.7 Hz, 1H), 4.68-4.75 (m, 2H), 4.84 (d, J=4.0 Hz, 1H), 4.86 (d, J=2.6 Hz, 1H), 4.97 (t, J=9.7 Hz, 1H), 5.21 (t, J=9.7 Hz, 1H), 5.27 (d, J=3.7 Hz, 1H), 5.27-5.32 (m, 1H), 7.08 (dd, J=1.8, 8.1 Hz, 1H), 7.32 (t, J=7.2 Hz, 2H), 7.40 (t, J=7.5 Hz, 2H), 7.47 (d, J=8.1 Hz, 1H), 7.69-7.78 (m, 4H), 7.88 (d, J=7.5 Hz, 2H), 9.42 (s, 1H); IR (KBr) 3360, 3010, 2950, 1755, 1590, 1535, 1440, 1420, 1370, 1230, 1050, and 755 cm$^{-1}$; mass spectrum [(+) ESI], m/z 1069.2 (M+H)$^+$, 1086.2/1088.2 (M+NH$_4$)$^+$; Anal. Calcd. for C$_{51}$H$_{57}$ClN$_2$O$_{21}$·3.5 H$_2$O: C, 54.09; H, 5.70; N, 2.47, Found: C, 53.67; H, 5.11; N, 2.34.

EXAMPLE 4

4-Benzoyl-N-{2-chloro-5-[(2,2',3,3',4',6,6'-hepta-O-acetyl-β-D-maltosyl)-oxy-methyl]-phenyl}-benzamide The title compound was prepared as a white foam (0.240 g, 94%) from 2-chloro-5-(hepta-O-acetyl-β-D-maltosyl-oxymethyl)-phenylamine using p-benzoylbenzoic acid and a procedure similar to step 2 of Example 2, mp >84° C. (decomp.); $^1$H NMR (DMSO-d$_6$) δ 1.93 (s, 3H), 1.94 (s, 6H), 1.97 (s, 6H), 2.01 (s, 3H), 2.08 (s, 3H), 3.93-4.03 (m, 4H), 4.15 (dd, J=4.6, 12.3 Hz, 1H), 4.21 (dd, J=4.6, 12.1 Hz, 1H), 4.39 (dd, J=2.2, 11.9 Hz, 1H), 4.70 (ABq, J=12.7 Hz, Δδ=0.14, 2H), 4.74 (dd, J=8.1, 9.7 Hz, 1H), 4.86 (dd, J=4.0, 10.5 Hz, 1H), 4.90 (d, J=8.1 Hz, 1H), 4.98 (t, J=9.7 Hz, 1H), 5.21 (dd, J=9.7, 10.5 Hz, 1H), 5.28 (d, J=4.0 Hz, 1H), 5.31 (dd, J=8.6, 9.4 Hz, 1H), 7.22 (dd, J=2.0, 8.3 Hz, 1H), 7.52 (d, J=2.0 Hz, 1H), 7.55-7.62 (m, 3H), 7.69-7.74 (m, 3H), 7.76-7.80 (m, 3H), 7.85-7.88 (m, 2H), 8.11-8.14 (m, 2H), 10.30 (s, 1H); IR (KBr) 3400, 3010, 2950, 1755, 1675, 1650, 1590, 1530, 1440, 1420, 1370, 1230, 1130, and 1040 cm$^{-1}$; mass spectrum [(+) FAB], m/z 984/986 (M+H)$^+$, 1006/1008 (M+Na)$^+$; Anal. Calcd. for C$_{47}$H$_{50}$ClNO$_{20}$: C, 57.35; H, 5.12; N, 1.42, Found: C, 57.11; H, 5.03; N, 1.32.

EXAMPLE 5

(4-Chloro-3-nitro-benzyl)-hepta-O-acetyl-1-thio-β-D-maltoside

To a stirred solution of hepta-O-acetyl-1-thio-β-maltose (2.0 g, 3.065 mmol) [P. L. Durette; T. Y. Shen. *Carb. Res.* 1978, 67, 484-490.] in acetone (20 ml) were added 4-chloro-3-nitrobenzyl bromide (0.844 mg, 3.37 mmol) and a solution of potassium carbonate (0.423 mg, 3.065 mmol) in water (10 ml). The mixture was boiled under reflux for 30 min, cooled and concentrated. The residue was extracted with dichloromethane, and the combined extracts were washed with water, and brine, dried (MgSO$_4$) and concentrated. Purification by flash chromatography (40%-60% EtOAc/petroleum ether gradient) afforded 1.588 g (63%) of the title compound as a white solid, mp 73-75° C.; $^1$H NMR (CDCl$_3$) δ 1.99 (s, 3H), 2.00 (s, 3H), 2.02 (s, 3H), 2.03 (s, 6H), 2.11 (s, 3H), 2.15 (s, 3H), 3.61-3.64 (m, 1H), 3.80 (d, J=13.6 Hz, 1H), 3.94-4.00 (m, 3H), 4.08 (dd, J=12.3, 2.4 Hz, 1H), 4.18-4.27 (m, 2H), 4.36 (d, J=9.9 Hz, 1H), 4.50 (dd, J=12.1, 2.6 Hz, 1H), 4.85 (dd, J=10.5, 4.0 Hz, 1H), 4.90 (apparant t, J=9.9 Hz, 1H), 5.05 (apparant t, J=9.9 Hz, 1H), 5.23 (apparant t, J=9.2 Hz, 1H), 5.34 (apparant t, J=9.7 Hz, 1H), 5.40 (d, J=4.0 Hz, 1H), 7.47 (dd, J=8.4, 2.0 Hz, 1H), 7.51 (d, J=8.4 Hz, 1H), 7.87 (d, J=2.0, Hz, 1H); IR (KBr) 3500, 2950, 1750, 1250 and 1050 cm$^{-1}$; mass spectrum [(+) FAB], m/z 822 (M+H)$^+$, 844 (M+Na)$^+$; Anal. Calcd. for C$_{33}$H$_{40}$ClNO$_{19}$S: C, 48.21; H, 4.90; N, 1.70, Found: C, 47.75; H, 4.86; N, 1.65.

EXAMPLE 6

(3-Amino-4-chloro-benzyl) hepta-O-acetyl-1-thio-β-D-maltoside

The title compound was prepared as a white solid from (4-chloro-3-nitro-benzyl)-hepta-O-acetyl-1-thio-β-D-maltoside using a procedure similar to step 1 of Example 2, mp 78° C.; $^1$H NMR (CDCl$_3$) δ 1.99 (s, 9H), 2.02 (s, 3H), 2.03 (s, 3H), 2.11 (s, 3H), 2.18 (s, 3H), 3.57-3.60 (m, 1H), 3.73 (ABq, J=13.0 Hz, Δδ=0.16, 2H), 3.95-4.08 (m, 3H), 4.17 (bs, 2H), 4.23 (d, J=4.2, Hz, 2H), 4.27 (dd, J=7.7, 4.4 Hz, 1H), 4.31 (d, J=4.4, Hz, 1H), 4.34 (d, J=10.1, Hz, 1H), ), 4.44 (dd, J=12.1, 3.3 Hz, 1H), ), 4.84 (dd, J=10.5, 4.0 Hz, 1H), 4.88 (apparant t, J=9.9 Hz, 1H), 5.03 (apparant t, J=9.9 Hz, 1H), 5.35 (apparant t, J=9.0 Hz, 1H), 5.35 (apparant t, J=9.4 Hz, 1H), 5.40 (d, J=4.0, Hz, 2H), 6.60 (dd, J=8.1, 2.0 Hz, 1H), 6.73 (d, J=2.0 Hz, 1H), 7.18 (d, J=8.13 Hz, 1H); IR (KBr) 3500, 2950, 1750, 1245 and 1050 cm$^{-1}$; mass spectrum [(−) FAB], m/z 790 (M−H)$^-$; Anal. Calcd. for C$_{33}$H$_{42}$ClNO$_{17}$: C, 50.03; H, 5.34; N, 1.77, Found: C, 49.55; H, 5.21; N, 1.71.

EXAMPLE 7

N-{2-Chloro-5-[hepta-O-acetyl-β-D-maltosyl-1-thio)-methyl]-phenyl}-acetamide The title compound was prepared as a white solid from (3-amino-4-chloro-benzyl) hepta-O-acetyl-1-thio-β-D-maltoside using a procedure similar to step 1 of Example 9, mp 80-81° C.; $^1$H NMR (CDCl$_3$) δ 1.99 (s, 9H), 2.03 (s, 6H), 2.11 (s, 3H), 2.16 (s, 3H), 2.25 (s, 3H), 3.61-3.65 (m, 1H), 3.82 (ABq, J=13.2 Hz, Δδ=0.14, 2H), 3.94-4.11 (m, 3H), 4.34 (d J=10.1 Hz, 1H), 4.53 (dd, J=12.3, 2.6 Hz, 1H), 4.83-4.91 (m, 2H), 5.05 (apparant t, J=9.7 Hz, 1H), 5.20 (apparant t, J=9.0

Hz, 1H), 5.34 (apparant t, J=10.3 Hz, 1H), 5.39 (d, J=4.2 Hz, 1H), 7.00 (dd, J=8.1, 2.2 Hz, 1H), 7.33 (d, J=8.4 Hz, 1H), 7.62 (s, 1H), 8.31 (s, 1H); IR (KBr) 3400, 2955, 1750, 1245 and 1050 cm$^{-1}$; mass spectrum [(+) FAB], m/z 834 (M+H)$^+$, 856 (M+Na)$^+$; Anal. Calcd. for $C_{35}H_{44}ClNO_{18}$ S: C, 50.39; H, 5.32; N, 1.68, Found: C, 49.99; H, 5.07; N, 1.59.

EXAMPLE 8

5-[(Hepta-O-acetyl-β-D-maltosyl)-oxy-methyl]-2-cyano-1-nitrobenzene

Step 1

α-Bromo-2-nitro-p-tolunitrile

A stirred mixture containing 4-methyl-2-nitrobenzonitrile (2.04 g, 12.6 mmol), N-bromosuccinimide (2.24 g, 12.6 mmol) and azobisisobutyronitrile (0.103 g, 0.630 mmol) in $CCl_4$ (50 mL) was irradiated with a 300 watt flood light for 2 h. The reaction was diluted with $CH_2Cl_2$ (50 ml), filtered and concentrated. Purification by flash chromatography (35 and 40% ether/pet. ether gradient) gave 1.44 g (47%) of the title compound as a yellow oil. $^1$H NMR (DMSO-d$_6$) δ 4.90 (s, 2H), 8.05 (dd, J=8.0, 1.5 Hz, 1H), 8.18 (d, J=8.0, 1H), 8.52 (s, 1H).

Step 2

α-Hydroxy-2-nitro-p-tolunitrile

A stirred solution containing α-bromo-2-nitro-p-tolunitrile (1.228 g, 5.095 mmol) and sodium formate (0.8664 g, 12.74 mmol) in ethanol:water (4:1, 25 mL) was refluxed for 2 h. The reaction was cooled to room temperature, diluted with 20% $CH_2Cl_2$/EtOAc, washed with H2O (3×), dried (MgSO$_4$) and concentrated. Purification by flash chromatography (1,2 and 3% MeOH/CHCl$_3$ gradient) gave 0.695 g (77%) of the title compound as a white solid. $^1$H NMR (DMSO-d$_6$) δ 4.71 (d, 2H), 5.75 (t, 1H), 7.89 (dd, J=7.9 Hz, 1H), 8.14 (d, J=7.9 Hz, 1H), 8.32 (s, 1H).

Step 3

5-[(Hepta-O-acetyl-β-D-maltosyl)-oxy-methyl]-2-cyano-1-nitrobenzene

At ambient temperature, to a stirred solution of acetobromomaltose (2.39 g, 3.41 mmol), α-hydroxy-2-nitro-p-tolunitrile (0.789 g, 4.43 mmol) and HgBr$_2$ (1.60 g, 4.43 mmol) in freshly distilled CH$_3$CN (34 mL) was added in one portion Hg(CN)$_2$ (1.12 g, 4.43 g, mmol). After 16 h, brine (50 mL) was added and the mixture was extracted with 10% $CH_2Cl_2$/EtOAc. The combined organic extracts were washed with brine (3×), dried (MgSO4) and concentrated. Purification by flash chromatography (1,2 and 3% MeOH/CHCl$_3$ gradient) gave 1.941 g (71%) of the title compound as a foam. An analytical sample was obtained by recrystallization from EtOAc/Hexane followed by recrystallization from EtOH to give a white solid, mp 155-157° C.; $^1$H NMR (DMSO-d$_6$) δ 1.93 (s, 3H), 1.94 (s, 3H), 1.97 (s, 3H), 1.99 (s, 3H), 2.01 (s, 3H), 2.06 (s, 3H), 3.93-4.01 (m, 4H), 4.36 (d, J=11.0 Hz, 1H), 4.77 (dd, J=9.6, 8.0 Hz, 1H), 4.83-4.88 (m, 2H), 4.93-5.00 (m, 3H), 5.21 (dd, J=10.3, 9.7 Hz, 1H), 5.27 (d, J=3.7 Hz, 1H), 5.30-5.34 (m, 1H), 7.84 (dd, J=7.9, 1.5 Hz, 1H), 8.18 .(d, J=7.9 Hz, 1H), 8.27 (s, 1H); IR (KBr) 3450, 2950, 2225, 1750, 1225 and 1050 cm$^{-1}$; mass spectrum [(+) FAB], m/z 797 (M+H)$^+$; Anal. Calcd. for $C_{34}H_{40}N_2O_{20}$: C, 51.26; H, 5.06; N, 3.52, Found: C, 51.06; H, 5.02; N, 3.31.

EXAMPLE 9

N-[2-Chloro-5-(β-D-maltosyl-oxymethyl)-phenyl]-adetamide

Step 1

N-[2-Chloro-5-(hepta-O-acetyl-β-D-maltosyl-oxymethyl)-phenyl]-

To a stirred solution of 2-chloro-5-(hepta-O-acetyl-β-D-maltosyl-oxymethyl)-phenylamine (20.6 g, 26.5 mmol) and triethylarnine (8.13 mL, 58.3 mmol) in THF (265 mL) at 0° C. was added dropwise acetyl chloride (2.26 mL, 31.8 mmol). After 0.5 h at this temperature, it was warmed to rt and stirred an additional 6 h. At this point, the reaction was concentrated and taken up in EtOAc (700 mL). This organic solution was washed with 1 N HCl (70 mL), sat. aq. NaHCO$_3$ (70 mL), and brine (70 mL) and then dried (MgSO$_4$). After concentration, the residue was purified by flash chromatography (20:80 to 100:0 EtOAc:petroleum ether gradient) to afford the product (16.2 g, 75%) as a glassy solid, mp 84-86° C.; $^1$H NMR (CDCl$_3$) δ 2.00 (s, 6H), 2.020 (s, 3H), 2.027 (s, 3H), 2.03 (s, 3H), 2.11 (s, 3H), 2.16 (s, 3H), 2.24 (s, 3H), 3.66-3.69 (m, 1H), 3.94-3.98 (m, 1H), 4.00-4.06 (m, 2H), 4.22-4.28 (m, 2H), 4.50-4.61 (m, 3H), 4.80-4.91 (m, 3H), 5.05 (t, J=10.1 Hz, 1H), 5.22 (t, J=9.2 Hz, 1H), 5.35 (dd, J=9.4, 10.5 Hz, 1H), 5.41 (d, J=4.0 Hz, 1H), 6.99 (dd, J=2.0, 8.1 Hz, 1H), 7.34 (d, J=8.1 Hz, 1H), 7.62 (s, 1H), 8.32 (s, 1H); IR (KBr) 3400, 2950, 1750, 1690, 1600, 1540, 1425, 1375, 1230 and 1050 cm$^{-1}$; mass spectrum [(+) ESI], m/z 818/820 (M+H)$^+$, 840 (M+Na)$^+$; Anal. Calcd. for $C_{35}H_{44}ClNO_{19}$: C, 51.38; H, 5.42; N, 1.71, Found: C, 51.03; H, 5.36; N, 1.59.

Step 2

N-[2-Chloro-5-(β-D-maltosyl-oxymethyl)-phenyl]-acetamide

A solution containing N-[2-chloro-5-(hepta-O-acetyl-β-D-maltosyl-oxymethyl)-phenyl]-acetamide (0.945 g, 1.12 mmol) and 25 weight % NaOMe in MeOH (19.2 μL, 0.336 mmol) in MeOH (27.6 ml) was refluxed for 2.5 h. The reaction was cooled to room temperature and concentrated, and the resulting residue was triturated with Et$_2$O to afford the product (0.583 g, 99%) as a foam; $^1$H NMR (DMSO-d$_6$) δ 2.07 (s, 3H), 3.03-3.16 (m 2H), 3.19-3.49 (m, 7H), 3.55-3.62 (m, 2H), 3.67-3.73 (m, 1H), 4.28 (d, J=7.7 Hz, 1H), 4.33-5.76 (bs, 7H), 4.67 (ABq, J=12.5 Hz, Δδ=0.22, 2H), 5.01 (d, J=3.7 Hz, 1H), 7.21 (dd, J=1.8, 8.1 Hz, 1H), 7.44 (d, J=8.1 Hz, 1H), 7.64 (d, J=1.5 Hz, 1H), 9.33-9.69 (bs, 1H); IR (KBr) 3400, 2900, 1680, 1600, 1540, 1430, 1375, 1310, 1150 and 1035 cm$^{-1}$; mass spectrum [(+) ESI], m/z 524/526 (M+H)$^+$, 546 (M+Na)$^+$; Anal. Calcd. for $C_{21}H_{30}ClNO_{12}$·1.0 MeOH: C, 47.53; H, 6.16; N, 2.52, Found: C, 47.94; H, 6.34; N, 2.42.

EXAMPLE 10

N-{5-[6,6'-Di-O-(tert-butyl-dimethyl-silyl)-β-D-maltosyloxy-methyl]-2-methyl-phenyl}-acetamide To a stirred solution of N-[5-(β-D-maltosyl-oxymethyl)-2-methyl-phenyl]-acetanide (prepared from 4-methyl-3-nitrobenzyl alcohol and acetobromomaltose using procedures similar to Example 1, Example 2—step 1, and Example 9) (1.5 g, 2.98 mmol) in CH$_2$Cl$_2$:DMF (1:1, 12 mL) at rt was added DMAP (0.109 g, 0.892 mmol) followed by triethylamine (1.66 mL, 11.9 mmol), and then finally TBDMSCl (1.35 g, 8.96 mmol). After 18, the solvent was removed on high vac and the residue diluted with EtOAc (200 mL). This organic layer was washed with 1 N HCl (20 mL), sat. aq. NaHCO$_3$ (20 mL), and brine (20 nlL) and then dried (MgSO$_4$). After concentration, the residue was purified by flash chromatography (0:100 to 25:75 MeOH:CHCl$_3$ gradient) to afford the product (16.2 g, 75%) as a white foam, mp 111-114° C.; $^1$H NMR (CDCl$_3$) δ 0.067 (s, 6H), 0.080 (s, 3H), 0.084 (s, 3H), 0.89 (s, 9H), 0.90 (s, 9H), 2.07 (s, 3H), 2.16 (s, 3H), 3.25-3.28 (m, 1H), 3.34-3.38 (m, 1H), 3.45-3.52 (m, 3H), 3.65-3.78 (m, 4H), 3.84-3.94 (m, 4H), 4.28 (d, J=7.7 Hz, 1H), 4.64 (ABq, J=12.1 Hz, Δδ=0.27, 2H), 4.65-4.69 (bs, 1H), 4.74-4.78 (m, 1H), 4.97 (d, J=3.3 Hz, 1H), 5.25-5.30 (m, 1H), 5.63-5.68 (bs, 1H), 6.99 (d, J=7.9 Hz, 1H), 7.07 (d, J=7.7 Hz, 1H), 7.54 (s, 1H), 7.59-7.63 (bs, 1H); IR (KBr) 3400, 2930, 2870, 1670, 1600, 1550, 1450, 1375, 1255, 1125, 1050, 840, and 790 cm$^{-1}$; mass spectrum [(+) FAB], m/z 754 (M+Na)$^+$; Anal. Calcd. for C$_{34}$H$_{61}$NO$_{12}$Si$_2$·0.5 H$_2$O: C, 55.11; H, 8.43; N, 1.89, Found: C, 54.91; H, 8.36; N, 1.85.

EXAMPLE 11

N-{2-Chloro-5-[6,6'-di-O-(tert-butyl-dimethyl-silvl)-β-D-maltosyloxy-methyl]-phenyl}-acetamide The title compound was prepared as a white foam (0.845 g, 59%) from N-[2-chloro-5-(β-D-maltosyl-oxymethyl)-phenyl]-acetamide using a procedure similar to Example 10, mp 93-98° C.; $^1$H NMR (CDCl$_3$) δ 0.07 (s, 12H), 0.88 (s, 9H), 0.89 (s, 9H), 2.18 (s, 3H), 3.25-3.31 (m, 1H), 3.41-3.46 (m, 1H), 3.49-3.58 (m, 3H), 3.69-3.79 (m, 4H), 3.85 (d, J=4.0 Hz, 1H), 3.87-3.92 (m, 2H), 3.92 (d, J=2.6 Hz, 1H), 4.32 (d, J=7.7 Hz, 1H), 4.53-4.58 (m, 1H), 4.68 (ABq, J=12.5 Hz, Δδ=0.25, 2H), 4.71-4.75 (m, 1H), 5.00 (d, J=3.5 Hz, 1H), 5.25 (dd, J=2.0, 6.4 Hz, 1H), 5.69 (s, 1H), 6.98-7.04 (m, 1H), 7.25-7.29 (m, 1H), 7.66 (s, 1H), 8.25 (s, 1H); IR (KBr) 3400, 2930, 2880, 1675, 1600, 1550, 1460, 1420, 1365, 1250, 1050, 850, and 800 cm$^{-1}$; mass spectrum [(+) FAB], m/z 774/776 (M+Na)$^+$; Anal. Calcd. for C$_{33}$H$_{58}$ClNO$_{12}$Si$_2$·0.5 H$_2$O: C, 52.05; H, 7.81; N, 1.84, Found: C, 52.16; H, 7.82; N, 1.80.

EXAMPLE 12

N-{2-Chloro-5-[([6,6'-di-O-benzoyl-β-D-maltosyl]oxy)methyl]phenyl}-acetamide

To a stirred solution of N-[2-chloro-5-(β-D-maltosyl-oxymethyl)-phenyl]-acetamide (1.00 g, 1.91 mmol) in THF (20.0 mL) at –40° C. was added collidine (20.0 mL, 151 mmol) followed by dropwise addition of benzoyl chloride (0.532 mL, 4.58 mmol). After 2 h at this temperature, it was warmed to rt and stirred an additional 18 h. At this point, the solvent was distilled off using the high vac, and the residue was purified by flash chromatography (2% to 20% MeOH:CHCl$_3$ gradient) to afford the product (0.500 g, 36%) as a glassy white solid, mp 99-100° C.; $^1$H NMR (CDCl$_3$) δ 2.12 (s, 3H), 3.41-3.51 (m, 3H), 3.59-3.68 (m, 2H), 3.77 (t, J=9.2 Hz, 1H), 3.85 (t, J=9.2 Hz, 1H), 4.06-4.12 (m, 1H), 4.30-4.34 (m, 2H), 4.40-5.35 (bs, 3H), 4.51 (dd, J=5.3, 12.1 Hz, 1H), 4.57 (ABq, J=12.5 Hz, Δδ=0.22, 2H), 4.59 (d, J=10.5 Hz, 1H), 4.80 (d, J=11.0 Hz, 1H), 5.07 (d, J=3.1 Hz, 1H), 5.45-5.66 (bs, 1H), 5.75-5.95 (bs, 1H), 6.86 (dd, J=1.3, 8.3 Hz, 1H), 7.12 (d, J=8.3 Hz, 1H), 7.23 (t, J=7.7 Hz, 2H), 7.33-7.52 (m, 4H), 7.70 (s, 1H), 7.91-7.96 (m, 4H), 8.14 (s, 1H); IR (KBr) 3400, 2900, 1720, 1620, 1600, 1550, 1450, 1425, 1375, 1320, 1225, 1100, and 1060 cm$^{-1}$; mass spectrum [(+) FAB], m/z 732 (M+H)$^+$, 754 (M+Na)$^+$; Anal. Calcd. for C$_{35}$H$_{38}$ClNO$_{14}$·0.5 H$_2$O: C, 56.72; H, 5.30; N, 1.89, Found: C, 56.62; H, 5.04; N, 1.90.

EXAMPLE 13

N-{2-Chloro-5-[([6,6'-di-O-benzoyl-2,2',3,3',4'-penta-acetyl-β-D-maltosyl]oxy)methyl]phenyl}-acetamide To a stirred solution of N-{5-[([6,6'-di-O-benzoyl-β-D-maltosyl]oxy)methyl]-2-chlorophenyl}-acetamide (0.122 g, 0.167 mmol) and triethylamine (0.256 mL, 1.84 mmol) in CH$_2$Cl$_2$ (5.0 mL) at rt was added dropwise acetic anhydride (0.0865 mL, 0.916 mmol) followed by a catalytic amount of DMAP (0.0102 g, 0.0835 mmol). After 18 h, the mixture was diluted with EtOAc (50 mL). This layer was washed with 1 N HCl (5 mL), sat. aq. NaHCO$_3$ (5 mL), and brine (5 mL) and then dried (MgSO$_4$). After concentration, the residue was purified by flash chromatography (2% to 20% acetone:CHCl$_3$ gradient) to afford the product (1.68 g, 94%) as a fine white powder (0.120 g, 76%), mp 97-100° C.; $^1$H NMR (CDCl$_3$) δ 1.96 (s, 3H), 1.99 (s, 3H), 2.01 (s, 3H), 2.03 (s, 3H), 2.04 (s, 3H), 2.22 (s, 3H), 3.80-3.84 (m, 1H), 4.06-4.10 (m, 1H), 4.18-4.22 (m, 3H), 4.53 (dd, J=4.0, 12.3 Hz, 1H), 4.58 (d, J=9.7 Hz, 1H), 4.61 (d, J=5.1 Hz, 1H), 4.76-4.79 (m, 1H), 4.79-4.82 (m, 1H), 4.86 (dd, J=4.0, 10.5 Hz, 1H), 4.92 (dd, J=7.7, 9.2 Hz, 1H), 5.15 (t, J=9.9 Hz, 1H), 5.27 (t, J=9.0 Hz, 1H), 5.41 (dd, J=9.7, 10.3 Hz, 1H), 5.47 (d, J=4.2 Hz, 1H), 6.95 (dd, J=1.8, 8.1 Hz, 1H), 7.29 (d, J=8.3 Hz, 1H), 7.41-7.50 (m, 4H), 7.52-7.62 (m, 3H), 7.98-8.01 (m, 2H), 8.07-8.09 (m, 2H), 8.30 (s, 1H); IR (KBr) 3400, 2950, 1760, 1725, 1620, 1600, 1550, 1450, 1425, 1375, 1275, 1245, 1120, 1050, and 710 cm$^{-1}$; mass spectrum [(+) FAB], m/z 942 (M+H)$^+$, 964 (M+Na)$^+$; Anal. Calcd. for C$_{45}$H$_{48}$ClNO$_{19}$·2.0 H$_2$O: C, 55.25; H, 5.36; N, 1.43, Found: C, 55.18; H, 4.87; N, 1.36.

EXAMPLE 14

(4-Chloro-3-nitrophenyl)methyl-4-O-[6-O-(3-pyridinylcarbonyl)-α-D-glucopyranosyl]-β-D-glucopyranoside-6-(3-pyridinecarboxylate)

To a stirred solution of N-[2-chloro-5-(β-D-maltosyl-oxymethyl)-phenyl]-acetamide (0.500 g, 0.977 mmol) in THF (9.8 mL) at –40° C. was added collidine (9.8 mL, 74.3 mmol) dropwise followed by nicotinoyl chloride hydrochloride (0.417 g, 2.34 mmol). After 2 h at this temperature, it was warmed to rt and stirred an additional 42 h. At this point, the reaction was concentrated on high vacuum and then diluted with EtOAc (250 mL). The solid was filtered off and washed with additional EtOAc (50 mL). The filtrate was concentrated, and the resulting oily residue purified by flash chromatography (40:2:1 to 10:2:1 EtOAc:EtOH:H$_2$O gradient) to afford the product (0.159 g, 23%) as a white solid, mp 145-147° C.; $^1$H NMR (DMSO-d$_6$) δ 3.15-3.25 (m, 2H), 3.32-3.35 (m, 1H), 3.43 (dd, J=5.3, 9.2 Hz, 1H), 3.45-3.52 (m, 1H), 3.54 (t, J=8.8 Hz, 1H), 3.70-3.76 (m, 1H), 3.91 (ddd, J=1.3, 5.5, 9.7 Hz, 1H), 4.29-4.38 (m, 2H), 4.41 (d, J=7.7 Hz, 1H), 4.53-4.58 (m, 1H), 4.67-4.72 (m, 1H), 4.72 (ABq, J=13.6 Hz, Δδ=0.07, 2H), 5.11 (d, J=4.8 Hz, 2H), 5.35 (d, J=5.7 Hz, 1H), 5.42 (d, J=5.1 Hz, 1H), 5.70 (d, J=2.6 Hz, 1H), 5.74 (d, J=5.9 Hz, 1H), 7.42 (ddd, J=0.6, 4.8, 7.9 Hz, 1H), 7.50 (ddd, J=0.7, 4.8, 7.9 Hz, 1H), 7.62 (dd, J=1.8, 8.3 Hz, 1H), 7.67 (d, J=8.3 Hz, 1H), 8.01 (d, J=1.8 Hz, 1H), 8.16 (tt, J=2.0, 8.6 Hz, 2H), 8.66 (dd, J=1.8, 4.8 Hz, 1H), 8.77 (dd, J=1.8, 4.8 Hz, 1H), 8.97 (dt, J=1.3, 9.2 Hz, 2H); IR (KBr) 3480, 3390, 3110, 2900, 1725, 1590, 1550, 1475, 1420, 1390, 1360, 1340, 1285, 1175, 1140, 1090, 1050, and 1015 cm$^{-1}$; mass spectrum [(+) FAB], m/z 722/724 (M+H)+, 744/746 (M+Na)+; Anal. Calcd. for $C_{31}H_{32}ClN_3O_{15} \cdot 1.5 H_2O$: C, 49.71; H, 4.71; N, 5.61, Found: C, 49.68; H, 4.53; N, 5.59.

EXAMPLE 15

(4-Chloro-3-nitrophenyl)methyl-4-O-[6-O-(3-pyridinylcarbonyl)-α-D-glucopyranosyl]-β-D-glucopyranoside The title compound was prepared as a white glass (0.070 g, 10%) from N-[2-chloro-5-(β-D-maltosyl-oxymethyl)-phenyl]-acetarride using a procedure similar to Example 14, mp >85° C. (decomp.); $^1$H NMR (DMSO-$d_6$) δ 3.07-3.14 (m, 1H), 3.14-3.23 (m, 1H), 3.25-3.36 (m, 2H), 3.36-3.47 (m, 3H), 3.51-3.58 (m, 1H), 3.67-3.73 (m, 1H), 3.83-3.89 (m, 1H), 4.29-4.34 (m, 2H), 4.54-4.62 (m, 2H), 4.79 (ABq, J=13.4 Hz, Δδ=0.17, 2H), 5.05-5.08 (m, 2H), 5.31 (d, J=5.7 Hz, 1H), 5.34 (d, J=5.1 Hz, 1H), 5.56 (d, J=6.4 Hz, 1H), 5.59 (d, J=3.1 Hz, 1H), 7.56 (ddd, J=0.9, 4.8, 8.1 Hz, 1H), 7.71 (dd, J=2.0, 8.3 Hz, 1H), 7.75 (d, J=8.3 Hz, 1H), 8.09 (d, J=1.5 Hz, 1H), 8.33 (dt, J=1.8, 7.9 Hz, 1H), 8.81 (dd, J=1.8, 4.8 Hz, 1H), 9.10 (dd, 3=0.7, 2.0 Hz, 1H); IR (KBr) 3390, 2910, 1730, 1625, 1600, 1540, 1475, 1410, 1360, 1290, 1140, 1120, and 1040 cm$^{-1}$; mass spectrum [(+) FAB], m/z 617/619 (M+H)+; Anal. Calcd. for $C_{25}H_{29}ClN_2O_{14} \cdot 1.5 H_2O$: C, 46.63; H, 5.01; N, 4.35, Found: C, 46.58; H, 4.88; N, 4.26.

EXAMPLE 16

N-[2-Chloro-5-[[(4-O-α-D-glucopyranosyl-β-D-glucopyranosyl)oxy]methyl]phenyl]-3-pyridinecarboxamide Step 1

N-[2-Chloro-5-[[[2,3,6-tri-O-acetyl-4-O-(2,3,4,6-tetra-O-acetyl-α-D-glucopyranoysl)-β-D-glucopyranosyl]oxy]methyl]phenyl]-3-pyridinecarboxamide To a stirred solution of 2-chloro-5-(hepta-O-acetyl-β-D-maltosyl-oxymethyl)-phenylamine (0.200 g, 0.258 mmol) and triethylamine (0.119 mL, 0.851 mmol) in THF (3 mL) at 0° C. was added nicotinoyl chloride hydrochloride (0.0551 mg, 0.310 mmol). After 0.5 h at this temperature, it was warmed to rt and stirred an additional 18 h. At this point, the solid was filtered off and washed with additional THF (10 mL). The filtrate was then concentrated and taken up in EtOAc (100 mL). This organic solution was washed with $H_2O$ (10 mL) and brine (10 mL) and then dried ($Na_2SO_4$). After concentration, the residue was purified by preparatory plate chromatography (10:90 MeOH:$CHCl_3$) to afford the product (0.183 g, 80%) as a white foam, mp 83-86° C.; $^1$H NMR (CDCl$_3$) δ 1.99 (s, 3H), 2.00 (s, 3H), 2.02 (s, 3H), 2.03 (s, 3H), 2.04 (s, 3H), 2.10 (s, 3H), 2.16 (s, 3H), 3.67-3.72 (m, 1H), 3.93-3.98 (m, 1H), 4.04 (dd, J=2.2, 11.9 Hz, 2H), 4.25 (dt, J=3.7, 12.5 Hz, 2H), 4.53 (dd, J=2.9, 12.3 Hz, 1H), 4.60 (d, J=7.7 Hz, 1H), 4.64 (d, J=12.5 Hz, 1H), 4.83-4.93 (m, 3H), 5.05 (t, J=10.1 Hz, 1H), 5.23 (t, J=9.4 Hz, 1H), 5.34 (dd, J=9.7, 10.5 Hz, 1H), 5.41 (d, J=4.2 Hz, 1H), 7.07 (dd, J=2.0 Hz, 1H), 7.41 (d, J=8.1 Hz, 1H), 7.48 (ddd, J=0.9, 4.8, 7.9 Hz, 1H), 8.23 (ddd, J=1.5, 2.2, 7.9 Hz, 1H), 8.43 (s, 1H), 8.48 (d, J=2.0 Hz, 1H), 8.82 (dd, J=1.5, 4.8 Hz, 1H), 9.15 (dd, J=0.7, 2.2 Hz, 1H); IR (KBr) 3400, 2950, 1755, 1675, 1600, 1550, 1420, 1375, 1235, and 1050 cm$^{-1}$; mass spectrum [(+) FAB], m/z 881 (M+H)+, 903 (M+Na)+; Anal. Calcd. for $C_{39}H_{45}ClN_2O_{19} \cdot 2.0 H_2O$: C, 51.07; H, 5.38; N, 3.05, Found: C, 50.80; H, 4.83; N, 2.89.

Step 2

N-[2-Chloro-5-[[(4-O-α-D-glucopyranosyl-β-D-glucopyranosyl)oxy]methyl] phenyl]-3-pyridinecarboxamide The title compound was prepared as a white foam (1.97 g, 57%) from N-[2-chloro-5-[[[2,3,6-tri-O-acetyl-4-O-(2,3,4,6-tetra-O-acetyl-α-D-glucopyranoysl)-β-D-glucopyranosyl] oxy]methyl]phenyl]-3-pyridinecarboxamide using a procedure similar to step 2 of Example 9, mp >106° C. (decomp.); $^1$H NMR (DMSO-$d_6$) δ 3.02-3.13 (m, 2H), 3.19-3.29 (m, 2H), 3.31-3.39 (m, 1H), 3.39-3.50 (m, 3H), 3.55-3.63 (m, 2H), 3.70-3.76 (m, 1H), 4.09 (q, J=5.3 Hz, 1H), 4.31 (d, J=7.9 Hz, 1H), 4.49-4.55 (m, 2H), 4.60 (d, J=12.5 Hz, 1H), 4.84-4.91 (m, 3H), 5.01 (d, J=3.7 Hz, 1H), 5.26 (d, J=5.1 Hz, 1H), 5.43 (d, J=6.4 Hz, 1H), 5.52 (d, J=3.1 Hz, 1H), 7.35 (dd, J=2.0, 8.3 Hz, 1H), 7.54 (d, J=8.1 Hz, 1H), 7.56-7.60 (m, 2H), 8.31 (dt, J=2.0, 7.9 Hz, 1H), 8.77 (dd, J=1.5, 4.8 Hz, 1H), 9.12-9.14 (m, 1H), 10.34 (s, 1H); IR (KBr) 3390, 2910, 2320, 1660, 1590, 1525, 1475, 1450, 1420, 1360, 1310, 1190, 1140, 1080, and 1030 cm$^{-1}$; mass spectrum [(+) FAB], m/z 587 (M+H)+, 609 (M+Na)+; Anal. Calcd. for $C_{25}H_{31}ClN_2O_{12} \cdot 1.5 H_2O$: C, 48.90; H, 5.58; N, 4.56, Found: C, 49.18; H, 5.52; N, 4.32.

EXAMPLE 17

Benzoic acid 6-{4-chloro-3-[(pyridine-3-carbonyl)-amino]-benzyloxy}-4,5-dihydoxy-3-(3,4,5-trihydroxy-6-hydroxymethyl-tetrahydro-pyran-2-yloxy)-tetrahydro-pyran-2-ylmethyl ester hydrochloride To a stirred solution of (R)-N-[5-[[[6-O-benzoyl4-O-[4,6-O-(phenylmethylene)-α-D-glucopyranosyl]-β-D-glucopyranosyl]oxy]methyl]-2-chlorophenyl]-3-pyridinecarboxamide (check other inyention record for preparation) (0.275 g, 0.353 mmol) in MeOH (10 mL) at 0° C. was added 1.0 M HCl in Et$_2$O (0.388 mL, 0.388 mmol). After 10 min. at this temperature, it was warmed to rt and stirred an additional 15 min. The mixture was concentrated to a thin oil and then triturated with Et$_2$O (5 mL). At this point, the solid which formed was filtered off and washed with additional Et$_2$O (4×, 2 mL). The solid was then dried on the high vacuum to afford the product (0.200 g, 70%) as an off-white solid (86% pure, contaminated with 14% HCl salt of SM), mp >157° C. (decomp.); $^1$H NMR (DMSO-$d_6$) δ 3.09-3.19 (m, 2H), 3.24 (dd, J=3.7, 9.4 Hz, 1H), 3.34-3.41 (m, 1H), 3.41-3.65 (m, 5H), 3.71 (dd, J=6.8, 8.1 Hz, 1H), 4.20-5.04 (m, 12H), 5.05 (d, J=3.7 Hz, 1H), 7.28 (dd, J=2.0, 8.3 Hz, 1H), 7.46-7.55 (m, 4H), 7.60-7.66 (m, 1H), 7.82 (dd, J=5.1, 7.9 Hz, 1H), 7.94-7.99 (m, 2H), 8.58 (d, J=7.7 Hz, 1H), 8.90 (dd, J=1.5, 5.3 Hz, 1H), 9.23 (d, J=1.5 Hz, 1H), 10.54 (s, 1H); IR (KBr) 3400, 2910, 2850, 2110, 1720, 1690, 1630, 1590, 1530, 1440, 1420, 1320, 1275, 1120, 1070, 1050, 1025, and 715 cm$^{-1}$; mass spectrum [(+) ESI], m/z 691.2 (M–HCl+H)+; Anal. Calcd. for $C_{32}H_{35}ClN_2O_{13} \cdot HCl \cdot 0.5 H_2O$: C, 52.89; H, 5.06; N, 3.74, Found: C, 52.99; H, 5.27; N, 3.46.

EXAMPLE 18

(4-Chloro-3-nitro-benzyl)-1-deoxy-1-thio-β-D-maltoside

The title compound was prepared as a white solid from (4-chloro-3-nitro-benzyl)-hepta-O-acetyl-1-thio-β-D-maltoside using a procedure similar to step 2 of Example 9, mp 90-93° C.; $^1$H NMR (DMSO-$d_6$) δ 3.03-3.74 (m, 11H), 3.80 (d, J=6.2 Hz, 1H), 3.86 (d, J=13.4 Hz, 1H), 4.01-4.08 (m, 2H), 4.58 (bd, 2H), 4.98 (bd, 3H), 5.20-5.67 (bs, 3 H), 7.65-7.72 (m, 2H), 8.03 (d, J=1.76 Hz, 1H).IR (KBr) 3400, 2930, 1550, 1300 and 1075 cm$^{-1}$; mass spectrum [(−)FAB], m/z 526 (M−H)$^-$; Anal. Calcd. for $C_{19}H_{26}ClNO_{12}S \cdot H_2O$: C, 41.80; H, 5.13; N, 2.56, Found: C, 41.35; H, 4.89; N, 2.40.

EXAMPLE 19

N-{2-Chloro-5-[β-D-maltosyl-1-thio)-methyl]-phenyl}-acetamide

The title compound was prepared as a white solid from N-{2-chloro-5-[hepta-O-acetyl-β-D-maltosyl-1-thio)-methyl]-phenyl}-acetamide using a procedure similar to step 2 of Example 9, mp 120-125° C.; $^1$H NMR (CD$_3$OD-d$_4$) δ 2.17 (s, 3H), 3.23-3.33 (m, 3H), 3.41 (dd, J=9.9, 3.7, Hz, 1H), 3.52-3.83 (m, 8H), 3.89 (dd, J=12.3, 2.0, Hz, 1H), 4.00 (d, J=13.2 Hz, 1H), 4.20 (d, J=9.9 Hz, 1H), 5.15 (d, J=4.0 Hz, 1H), 7.20 (dd, J=8.4, 1.8, Hz, 1H), 7.37 (d, J=8.4 Hz, 1H), 7.74 (s, 1H); IR (KBr) 3400, 2900, 1600, 1550 and 1050 cm$^{-1}$; mass spectrum [(−)FAB)], m/z 538 (M−H)$^-$; Anal. Calcd. for $C_{21}H_{30}ClNO_{11}S \cdot 1.0\ H_2O$: C, 45.20; H, 5.78; N, 2.51, Found: C, 45.43; H, 5.62; N, 2.43.

EXAMPLE 20

5-{[6,6'-Bis-O-(4-toluenesulfonyl)-β-maltosyl]-oxy-methyl}-2-methyl-1-nitrobenzene Step 1

5-[(β-Maltosyl)-oxy-methyl]-2-methyl-1-nitrobenzene

A stirred solution containing 5-[(hepta-O-acetyl-β-maltosyl)-oxy-methyl]-2-methyl-1-nitrobenzene (prepared from 4-methyl-3-nitrobenzyl alcohol and acetobromomaltose using procedures similar to Example 1) (0.835 g, 1.06 mmol) and 25 weight % NaOMe/MeOH (0.115 g, 0.531 mmol) in MeOH (25 mL) was refluxed for 4 h. The reaction was cooled to ambient temperature and concentrated in vacuo. Purification by reverse phase BPLC (C18, 25% CH$_3$CN:H$_2$O) gave 0.380 g (73%) of the title compound as a white foam; $^1$H NMR (DMSO-d$_6$) δ 2.50 (s, 3H), 3.60-3.21 (m, 2H), 3.22-3.57 (m, 7H), 3.59-3.65 (m, 2H), 3.71-3.73 (m, 2H), 4.31 (d, 1H), 4.51-4.54 (m, 2H), 4.67 (d, 1H), 4.87-4.91 (m, 3H), 5.02 (d, 1H), 5.29 (d, 1H), 5.44 (d, 1H), 5.53 (d, 1H), 7.48 (d, 1H), 7.64 (dd, 1H), 8.01 (s, 1H).

Step 2

5-{[6,6'-Bis-O-(4-toluenesulfonyl)-β-maltosyl]-oxy-methyl}-2-methyl-1-nitrobenzene At 0° C., to a stirred solution of 5-[(β-maltosyl)-oxy-methyl]-2-methyl-1-nitrobenzene (0.380 g, 0.774 mmol) in pyridine (4.5 mL) was added portionwise a solution of p-toluenesulfonyl chloride (0.812 g, 4.25 mmol) in CH$_2$Cl$_2$ (4.5 mL), over a period of 5 h. The reaction was quenched with H$_2$O (30 mnL) and extracted with EtOAc. The combined organic extracts were washed successively with sat. aq. NaHCO3 (3×), with sat. aq. CuSO$_4$ (3×), with brine (3×), dried (Na$_2$SO$_4$) and concentrated. Purification by preparative HPLC (C18, 65% CH$_3$CN:H$_2$O) gave 0.373 g (59%) of the title compound as a white solid, mp 85-92° C.; $^1$H NMR (DMSO-d$_6$) δ 2.34 (s, 3H), 2.40 (s, 3H), 2.48 (s, 3H), 3.01-3.10 (m, 2H), 3.12-3.17 (m, 1H), 3.23-3.40 (m, 3H), 3.51-3.55 (m, 2H), 4.02-4.14 (m, 3H), 4.23-4.29 (m, 2H), 4.63 (ABq, J=13.1 Hz, Δδ=0.05, 2H), 4.92 (d, 1H), 5.01 (d, 1H), 5.22 (d, 1H), 5.36 (d, 1H), 5.48 (d, 1H), 5.54 (d, 1H), 7.39 (d, 2H), 7.45-7.48 (m, 3H), 7.60 (dd, 1H), 7.71-7.77 (m, 4H), 7.96 (s, 1H); IR (KBr) 3380, 2920, 1600, 1530, 1360 and 1175 cm$^{-1}$; mass spectrum [(+) FAB], m/z 822 (M+Na)$^+$; Anal. Calcd. for $C_{34}H_{41}NO_{17}S_2 \cdot H_2O$: C, 49.93; H, 5.17; N, 1.75, Found: C, 49.77; H, 4.94; N, 1.70.

EXAMPLE 21

5-{[2,2',3,3',4'-Penta-O-acetyl-6,6'-bis-O-(4-toluenesulfonyl)-β-maltosyl]-oxy-methyl}-2-methyl-1-nitrobenzene At 0° C., to a stirred solution containing 5-{[6,6'-bis-O-(4-toluenesulfonyl)-β-maltosyl]-oxy-methyl}-2-methyl-1-nitrobenzene (1.79 g, 2.24 mrmol), pyridine (5.43 mL, 67.1 mmol) and 4-dimethylaminopyridine (1.25 g, 11.2 mmol) was added dropwise acetic anhydride (2.09 mL, 22.4 mmol). After 3 h, the reaction eventually warmed to room temperature. The solution was diluted with diethyl ether (100 mL), washed successively with H$_2$O (2×), sat. aq. NaHCO$_3$ (2×), sat. aq. CuSO$_4$ (2×), brine (2×), dried (Na$_2$SO$_4$) and concentrated. Purification by flash chromatography (3, 4 and 5% MeOH:CHCl$_3$ gradient) gave 1.785 g, (79%), of the title compound as a white solid after crystallization from EtOAc: hexane, mp 83° C.; $^1$H NMR (DMSO-d$_6$) δ 1.910 (s, 3H), 1.918 (s, 3H), 1.920 (s, 3H), 1.924 (s, 3H), 1.932 (s, 3H), 2.36 (s, 3H), 2.42 (s, 3H), 2.51 (s, 3H), 3.66 (t; 1H), 3.86 (dd, 1H), 3.92-3.96 (m, 1H), 4.06 (dd, 1H), 4.16-4.29 (m, 3H), 4.51-4.60 (m, 2H), 4.64-4.72 (m, 2H), 4.79 (d, 1H), 4.89 (t, 1H), 5.06-5.13 (m, 2H), 5.24 (t, 1H), 7.43 (d, 2H), 7.47-7.50 (m, 4H), 7.74-7.77 (m, 4H), 7.84 (s, 1H); mass spectrum [(+) FAB], m/z 1010 (M+H)$^+$; Anal. Calcd. for $C_{44}H_{51}NO_{22}S_2$: C, 52.32; H, 5.09; N, 1.39, Found: C, 52.46; H, 5.15; N, 1.41.

EXAMPLE 22

5-{[6,6'-Dideoxy-6,6'-bis(4-nitro-imidazol-1-yl)-β-maltosyl]-oxy-methyl}-2-methyl-1-nitrobenzene At ambient temperature, to a stirred solution of 4-nitroimidazole (0.478 g, 4.23 mmol) in DMF (8 mL) was added K$_2$CO$_3$ (0.278 g, 2.01 mmol). After 0.5 h, to the reaction was added a solution of 5-{[6,6'-bis-O-(4-toluenesulfonyl)-β-maltosyl]-oxy-methyl}-2-methyl-1-nitrobenzene (1.61 g, 0.201 mmol) in DMF (20 mL) and the reaction was heated at 100° C. for 24 h. The reaction was concentrated in vacuo. Purification by reverse phase HPLC (C18, 30% CH$_3$CN:H$_2$O) gave 0.40 g (29%) of the title compound as a white solid, mp 146° C.; $^1$H NMR (DMSO-d$_6$) δ 2.48 (s, 3H), 2.89 (t, 1H), 3.08 (t, 1H), 3.20-3.29 (m, 2H), 3.40-3.47 (m, 2H), 3.64 (dt, 1H), 3.88 (dd, 1H), 3.974.03 (m, 2H), 4.21-4.27 (m, 2H), 4.43-4.47 (m, 2H), 4.59 (d, 1H), 5.11 (d, 1H), 5.17 (d, 1H), 5.40 (br. s, 1H), 5.57 (br. s, 1H), 5.68 (br. s, 1H), 5.84 (br. s, 1H), 7.41-7.46 (m, 2H), 7.65 (d, 1H), 7.74 (d, 1H), 7.85 (s, 1H), 8.22 (d, 1H), 8.25 (d, 1H); mass spectrum [(+) FAB], m/z 682 (M+H)$^+$; Anal. Calcd. for $C_{26}H_{31}N_7O_{15} \cdot 2\ H_2O$: C, 43.52; H, 4.92; N, 13.66, Found: C, 43.90; H, 4.72; N, 13.31.

EXAMPLE 23

5-{[2,2',3,3',4'-Penta-O-acetyl-6,6'-dideoxy-6,6'-bis(4-nitro-imidazol-1-yl)-β-maltosyl]-oxy-methyl}-2-methyl-1-nitrobenzene At ambient temperature, to a stirred solution of 4-nitroimidazole (0.177 g, 1.57 mmol) in DMF (3 mL) was added K$_2$CO$_3$ (0.103 g, 0.747 mmol). After 0.5 h, to the reaction was added a solution of 5-{[2,2',3,3',4'-penta-O-acetyl-6,6'-bis-O-(4-toluenesulfonyl)-β-maltosyl]-oxy-methyl}-2-methyl- 1-nitrobenzene (0.754 g, 0.747 mmol) in DMF (7 mL) and the reaction was heated at 100° C. for 4 h. At ambient temperature, the reaction was quenched with ice cold $H_2O$ (50 mL) and extracted with EtOAc. The organic extracts were dried ($Na_2SO_4$) and concentrated. Purification by flash chromatography (5, 6 and 7% $MeOH:CHCl_3$ gradient) gave 0.315 g, (47%), of the title compound as a white solid after crystallization from EtOAc:hexane, mp 140° C.; $^1H$ NMR (DMSO-$d_6$) δ 1.92 (s, 3H), 1.93 (s, 3H), 1.94 (s, 6H), 2.08 (s, 3H), 2.49 (s, 3H), 3.64 (dd, 1H), 3.91 (t, 1H), 4.00-4.06 (m, 1H), 4.27-4.40 (m, 5H), 4.54 (d, 1H), 4.74-4.79 (m, 3H), 4.96 (dd, 1H), 5.22-5.30 (m, 3H), 7.33 (dd, 1H), 7.43 (d, 1H), 7.69 (d, 1H), 7.72 (d, 1H), 7.77 (d, 1H), 8.26 (d, 1H), 8.34 (d, 1H); mass spectrum [(+) FAB], m/z 892 (M+H)$^+$; Anal. Calcd. for $C_{36}H_{41}N_7O_{20}$: C, 48.49; H, 4.63; N, 11.00, Found: C, 48.32; H, 4.52; N, 10.90.

What is claimed is:

1. A compound of formula I having the structure

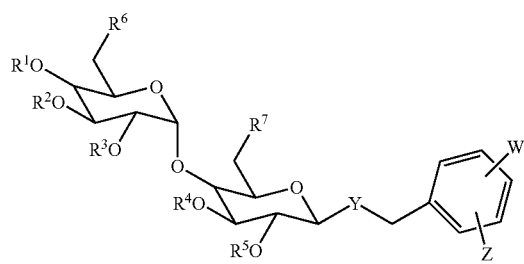

wherein $R^1$, $R^2$, $R^3$, $R^4$, and $R^5$ are each, independently, hydrogen, acyl of 2-7 carbon atoms, haloacyl of 2-7 carbon atoms, nitroacyl of 2-7 carbon atoms, cyanoacyl of 2-7 carbon atoms, trifluoromethylacyl of 3-8 carbon atoms, or benzoyl in which the phenyl moiety is substituted with $R^8$;

$R^6$ and $R^7$ are each, independently, —OH, —OR$^9$, O-tert-butyldimethylsilyl, O-trialkylsilyl of 1-6 carbon atoms per alkyl moiety, O-triphenylsilyl,

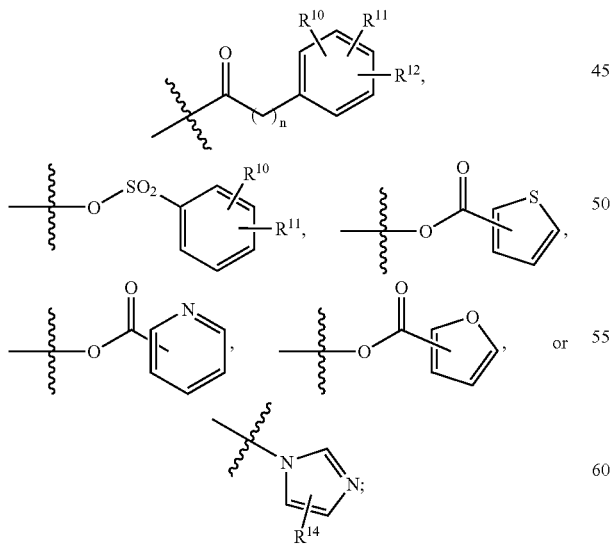

$R^8$, $R^{10}$, $R^{11}$, and $R^{12}$ are each, independently, hydrogen, —CN, —NO$_2$, halogen, CF$_3$, alkyl of 1-6 carbon atoms, acetyl, benzoyl, or alkoxy of 1-6 carbon atoms;

$R^9$ is acyl of 2-7 carbon atoms, haloacyl of 2-7 carbon atoms, nitroacyl of 2-7 carbon atoms, cyanoacyl of 2-7 carbon atoms, trifluoromethylacyl of 3-8 carbon atoms, or benzoyl in which the phenyl moiety is substituted with $R^8$;

Y is S, NH, NMe, or CH$_2$;

W is halogen, —CN, CF$_3$, alkyl of 1-6 carbon atoms, haloalkyl of 1-6 carbon atoms, nitroalkyl of 1-6 carbon atoms, cyanoalkyl of 1-6 carbon atoms, alkoxyalkyl of 2-12 carbon atoms, alkoxy of 1-6 carbon atoms, or phenyl mono-, di-, or tri-substituted with $R^8$;

Z is —NO$_2$, —NH$_2$, —NHR$^{13}$, or —NHCO-Het;

$R^{13}$ is acyl of 2-7 carbon atoms, haloacyl of 2-7 carbon atoms, nitroacyl of 2-7 carbon atoms, cyanoacyl of 2-7 carbon atoms, trifluoromethylacyl of 3-8 carbon atoms, benzoyl in which the phenyl moiety is substituted with $R^8$, or $R^{13}$ is an α-amino acid in which the a carboxyl group forms an amide with the nitrogen of Z, wherein if said amino acid is glutamic acid or aspartic acid, the non-α carboxylic acid is an alkyl ester in which the alkyl moiety contains from 1-6 carbon atoms;

Het is pyridyl substituted with $R^8$, thienyl substituted with $R^8$, furyl substituted with $R^8$, oxazolyl substituted with $R^8$, pyrazinyl substituted with $R^8$, pyrimidinyl substituted with $R^8$, or thiazolyl substituted with $R^8$;

$R^{14}$ is $R^8$, —NH$_2$, —CO$_2$H, or —NH-acyl of 2-7 carbon atoms;

n=0-3;

or a pharmaceutically acceptable salt thereof.

2. The compound according to claim 1, wherein $R^1$, $R^2$, $R^3$, $R^4$, and $R^5$ are each, independently, hydrogen or acyl of 2-7 carbon;

$R^6$ and $R^7$ are each, independently, —OH, —OR$_9$, O-tert-butyldimethylsilyl,

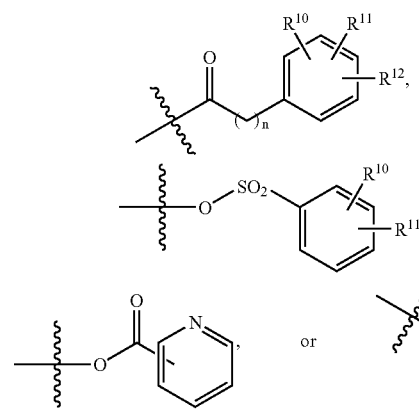

$R^9$ is acyl of 2-7 carbon atoms, or benzoyl in which the phenyl moiety is substituted with $R^8$;

Y is S; and $R^{13}$ is acyl of 2-7 carbon atoms, or benzoyl in which the phenyl moiety is substituted with $R^8$, or $R^{13}$ is an α-amino acid in which the α carboxyl group forms an amide with the nitrogen of Z, wherein if said amino acid is glutamic acid or aspartic acid, the non-α carboxylic acid is an alkyl ester in which the alkyl moiety contains from 1-6 carbon atoms.

3. The compound of claim 1 which is:
(4-Chloro-3-nitro-benzyl)-hepta-O-acetyl-1-thio-β-D-maltoside or a pharmaceutically acceptable salt thereof;
(3-Amino-4-chloro-benzyl)hepta-O-acetyl-1-thio-β-D-maltoside or a pharmaceutically acceptable salt thereof;
N-{2-chloro-5-[hepta-O-acetyl-β-D-maltosyl-1-thio)-methyl]-phenyl}-acetamide or a pharmaceutically acceptable salt thereof;
(4-Chloro-3-nitro-benzyl)-1-deoxy-1-thio-β-D-maltoside or a pharmaceutically acceptable salt thereof; or
N-{2-chloro-5-[β-D-maltosyl-1-thio)-methyl]-phenyl}-acetamide or a pharmaceutically acceptable salt thereof.

4. A pharmaceutical composition which comprises a compound of formula I having the structure

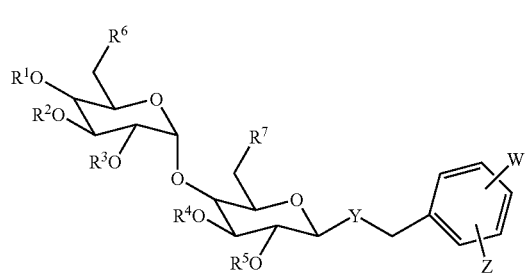

wherein
$R^1$, $R^2$, $R^3$, $R^4$, and $R^5$ are each, independently, hydrogen, acyl of 2-7 carbon atoms, haloacyl of 2-7 carbon atoms, nitroacyl of 2-7 carbon atoms, cyanoacyl of 2-7 carbon atoms, trifluoromethylacyl of 3-8 carbon atoms, or benzoyl in which the phenyl moiety is substituted with $R^8$;
$R^6$ and $R^7$ are each, independently, —OH, —$OR^9$, O-tert-butyldimethylsilyl, O-trialkylsilyl of 1-6 carbon atoms per alkyl moiety, O-triphenylsilyl,

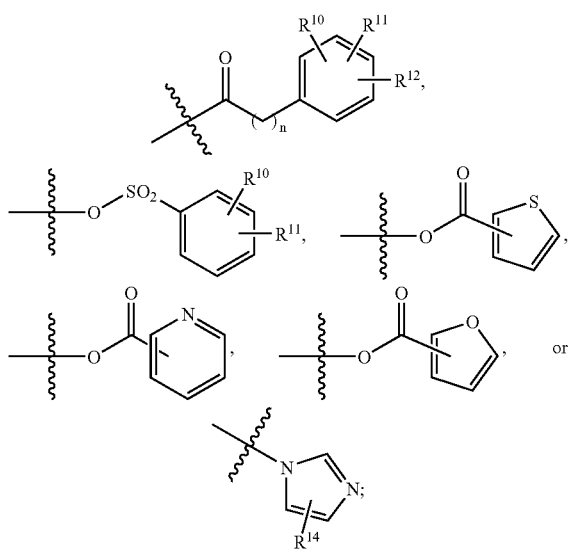

$R^8$, $R^{10}$, $R^{11}$, and $R^{12}$ are each, independently, hydrogen, —CN, —$NO_2$, halogen, $CF_3$, alkyl of 1-6 carbon atoms, acetyl, benzoyl, or alkoxy of 1-6 carbon atoms;
$R^9$ is acyl of 2-7 carbon atoms, haloacyl of 2-7 carbon atoms, nitroacyl of 2-7 carbon atoms, cyanoacyl of 2-7 carbon atoms, trifluoromethylacyl of 3-8 carbon atoms, or benzoyl in which the phenyl moiety is substituted with $R^8$;
Y is S, NH, NMe, or $CH_2$;
W is halogen, —CN, $CF_3$, alkyl of 1-6 carbon atoms, haloalkyl of 1-6 carbon atoms, nitroalkyl of 1-6 carbon atoms, cyanoalkyl of 1-6 carbon atoms, alkoxyalkyl of 2-12 carbon atoms, alkoxy of 1-6 carbon atoms, or phenyl mono-, di-, or tri-substituted with $R^8$;
Z is 13 $NO_2$, —$NH_2$, —$NHR^{13}$, or —NHCO-Het;
$R^{13}$ is acyl of 2-7 carbon atoms, haloacyl of 2-7 carbon atoms, nitroacyl of 2-7 carbon atoms, cyanoacyl of 2-7 carbon atoms, trifluoromethylacyl of 3-8 carbon atoms, benzoyl in which the phenyl moiety is substituted with $R^8$, or
$R^{13}$ is an α-amino acid in which the a carboxyl group forms an amide with the nitrogen of Z, wherein if said amino acid is glutamic acid or aspartic acid, the non-α carboxylic acid is an alkyl ester in which the alkyl moiety contains from 1-6 carbon atoms;
Het is pyridyl substituted with $R^8$, thienyl substituted with $R^8$, furyl substituted with $R^8$, oxazolyl substituted with $R^8$, pyrazinyl substituted with $R^8$, pyrimidinyl substituted with $R^8$, or thiazolyl substituted with $R^8$;
$R^{14}$ is $R^8$, —$NH_2$, —$CO_2H$, or —NH-acyl of 2-7 carbon atoms;
n=0-3;
or a pharmaceutically acceptable salt thereof, and a pharmaceutical carrier.

5. A compound selected from the group consisting of:
N-{5-[(Hepta-O-acetyl-β-D-maltosyloxy)-methyl]-2-chloro-phenyl}-L-aspartamide-γ-tert-butyl ester or a pharmaceutically acceptable salt thereof;
N-{2-Chloro-5-[(2,2',3,3',4',6,6')-hepta-O-acetyl-β-D-maltosyl-oxymethyl]-phenyl}-(9H-fluoren-9-yl-methoxycarbonyl)-L-alaninamide or a pharmaceutically acceptable salt thereof;
4-Benzoyl-N-{2-chloro-5-[(2,2',3,3',4',6,6'-hepta-O-acetyl-β-D-maltosyl)-oxy-methyl]-phenyl}-benzamide or a pharmaceutically acceptable salt thereof;
N-[2-Chloro-5-(β-D-maltosyl-oxymethyl)-phenyl]-acetamide or a pharmaceutically acceptable salt thereof;
N-{5-[6,6'-Di-O-(tert-butyl-dimethyl-silyl)-β-D-maltosyloxy-methyl]-2-methyl-phenyl}-acetamide or a pharmaceutically acceptable salt thereof;
N-{2-Chloro-5-[6,6'-di-O-(tert-butyl-dimethyl-silyl)-β-D-maltosyloxy-methyl]-phenyl}-acetamide or a pharmaceutically acceptable salt thereof;
N-{2-Chloro-5-[([6,6'-di-O-benzoyl-β-D-maltosyl]oxy) methyl]phenyl}-acetamide or a pharmaceutically acceptable salt thereof;
N-{2-Chloro-5-[([6,6'-di-O-benzoyl-2,2',3,3',4'-penta-acetyl-β-D-maltosyl]oxy)-methyl]phenyl}-acetamide or a pharmaceutically acceptable salt thereof;
(4-Chloro-3-nitrophenyl)methyl-4-O-[6-O-(3-pyridinyl-carbonyl)-α-D-glucopyranosyl]-β-D-glucopyranoside-6-(3-pyridinecarboxylate) or a pharmaceutically acceptable salt thereof;
(4-Chloro-3-nitrophenyl)methyl-4-O-[6-O-(3-pyridinyl-carbonyl)-α-D-glucopyranosyl]-β-D-glucopyranoside or a pharmaceutically acceptable salt thereof;
N-[2-Chloro-5-[[(4-O-α-D-glucopyranosyl-β-D-glucopyranosyl)oxy]methyl]phenyl]-3-pyridinecarboxamide or a pharmaceutically acceptable salt thereof;
Benzoic acid 6-{4-chloro-3-[(pyridine-3-carbonyl)-amino]-benzyloxy}-4,5-dihydoxy-3-(3,4,5-trihydroxy- 6-hydroxymethyl-tetrahydro-pyran-2-yloxy)-tetrahydro-pyran-2-ylmethyl ester or a pharmaceutically acceptable salt thereof;

5-{[6,6'-Bis-O-(4-toluenesulfonyl)-β-maltosyl]-oxy-methyl}-2-methyl-1-nitrobenzene or a pharmaceutically acceptable salt thereof;

5-{[2,2',3,3',4'-Penta-O-acetyl-6,6'-bis-O-(4-toluenesulfonyl)-β-maltosyl]-oxy-methyl}-2-methyl-1-nitrobenzene or a pharmaceutically acceptable salt thereof;

5-{[6,6'-Dideoxy-6,6'-bis(4-nitro-imidazol-1-yl)-β-maltosyl]-oxy-methyl}-2-methyl-1-nitrobenzene or a pharmaceutically acceptable salt thereof; and 5-{[2,2',3,3',4'-Penta-O-acetyl-6,6'-dideoxy-6,6'-bis(4-nitro-imidazol-1-yl)-β-maltosyl]-oxy-methyl}-2-methyl-1-nitrobenzene or a pharmaceutically acceptable salt thereof.

6. A pharmaceutical composition which comprises a compound selected from the group consisting of:

N-{5-[(Hepta-O-acetyl-β-D-maltosyloxy)-methyl]-2-chloro-phenyl}-L-aspartamide-γ-tert-butyl ester or a pharmaceutically acceptable salt thereof;

N-{2-Chloro-5-[(2,2',3,3',4',6,6')-hepta-O-acetyl-β-D-maltosyl-oxymethyl]-phenyl}-(9H-fluoren-9-yl-methoxycarbonyl)-L-alaninamide or a pharmaceutically acceptable salt thereof;

4-Benzoyl-N-{2-chloro-5-[(2,2',3,3',4',6,6'-hepta-O-acetyl-β-D-maltosyl)-oxy-methyl]-phenyl}-benzamide or a pharmaceutically acceptable salt thereof;

N-[2-Chloro-5-(β-D-maltosyl-oxymethyl)-phenyl]-acetamide or a pharmaceutically acceptable salt thereof;

N-{5-[6,6'-Di-O-(tert-butyl-dimethyl-silyl)-β-D-maltosyloxy-methyl]-2-methyl-phenyl}-acetamide or a pharmaceutically acceptable salt thereof;

N-{2-Chloro-5-[6,6'-di-O-(tert-butyl-dimethyl-silyl)-β-D-maltosyloxy-methyl]-phenyl}-acetamide or a pharmaceutically acceptable salt thereof;

N-{2-Chloro-5-[([6,6'-di-O-benzoyl-β-D-maltosyl]oxy)methyl]phenyl}-acetamide or a pharmaceutically acceptable salt thereof;

N-{2-Chloro-5-[([6,6'-di-O-benzoyl-2,2',3,3',4'-penta-acetyl-β-D-maltosyl]oxy)-methyl]phenyl}-acetamide or a pharmaceutically acceptable salt thereof;

(4-Chloro-3-nitrophenyl)methyl-4-O-[6-O-(3-pyridinyl-carbonyl)-α-D-glucopyranosyl)-β-D-glucopyranoside-6-(3-pyridinecarboxylate) or a pharmaceutically acceptable salt thereof;

(4-Chloro-3-nitrophenyl)methyl-4-O-[6-O-(3-pyridinyl-carbonyl)-α-D-glucopyranosyl]-β-D-glucopyranoside or a pharmaceutically acceptable salt thereof;

N-[2-Chloro-5-[[(4-O-α-D-glucopyranosyl-β-D-glucopyranosyl)oxy]methyl]phenyl]-3-pyridinecarboxamide or a pharmaceutically acceptable salt thereof;

Benzoic acid 6-{4-chloro-3-[(pyridine-3-carbonyl)-amino]-benzyloxy}-4,5-dihydoxy-3-(3,4,5-trihydroxy-6-hydroxymethyl-tetrahydro-pyran-2-yloxy)-tetrahydro-pyran-2-ylmethyl ester or a pharmaceutically acceptable salt thereof;

5-{[6,6'-Bis-O-(4-toluenesulfonyl)-β-maltosyl]-oxy-methyl}-2-methyl-1-nitrobenzene or a pharmaceutically acceptable salt thereof;

5-{[2,2',3,3',4'-Penta-O-acetyl-6,6'-bis-O-(4-toluenesulfonyl)-β-maltosyl]-oxy-methyl}-2-methyl-1-nitrobenzene or a pharmaceutically acceptable salt thereof;

5-{[6,6'-Dideoxy-6,6'-bis(4-nitro-imidazol-1-yl)-β-maltosyl]-oxy-methyl}-2-methyl-1-nitrobenzene or a pharmaceutically acceptable salt thereof; and 5-{[2,2',3,3',4'-Penta-O-acetyl-6,6'-dideoxy-6,6'-bis(4-nitro-imidazol-1-yl)-β-maltosyl]-oxy-methyl}-2-methyl-1-nitrobenzene or a pharmaceutically acceptable salt thereof; and a pharmaceutically acceptable carrier.

\* \* \* \* \*